(12) United States Patent
Lu et al.

(10) Patent No.: US 12,193,852 B2
(45) Date of Patent: Jan. 14, 2025

(54) SYSTEMS AND RELATED METHODS FOR STATIONARY DIGITAL CHEST TOMOSYNTHESIS (S-DCT) IMAGING

(71) Applicant: The University of North Carolina at Chapel Hill, Chapel Hill, NC (US)

(72) Inventors: Jianping Lu, Chapel Hill, NC (US); Jing Shan, Chapel Hill, NC (US); Yueh Lee, Chapel Hill, NC (US); Otto Z. Zhou, Chapel Hill, NC (US); Jabari Calliste, Chapel Hill, NC (US); Christina Inscoe, Holly Springs, NC (US); Pavel Chtcheprov, Chapel Hill, NC (US); Andrew Tucker, Cary, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 854 days.

(21) Appl. No.: 17/234,679

(22) Filed: Apr. 19, 2021

(65) Prior Publication Data
US 2021/0236067 A1 Aug. 5, 2021

Related U.S. Application Data

(63) Continuation of application No. 14/886,842, filed on Oct. 19, 2015, now Pat. No. 10,980,494.
(Continued)

(51) Int. Cl.
A61B 6/02 (2006.01)
A61B 6/00 (2024.01)
(Continued)

(52) U.S. Cl.
CPC ............... *A61B 6/025* (2013.01); *A61B 6/06* (2013.01); *A61B 6/4007* (2013.01); *A61B 6/482* (2013.01);
(Continued)

(58) Field of Classification Search
CPC ..... A61B 6/025; A61B 6/4007; A61B 6/4085; A61B 6/037
See application file for complete search history.

(56) References Cited

U.S. PATENT DOCUMENTS 2,842,706 A 7/1958 Dobischek et al.
3,617,285 A 11/1971 Staudenmayer
(Continued)

FOREIGN PATENT DOCUMENTS

CN 2336381 Y 9/1999
CN 2440535 8/2001
(Continued)

OTHER PUBLICATIONS

"Low-Dose and Scatter-Free Cone-Beam CT Imaging Using a Stationary Beam Blocker in a Single Scan: Phantom Studies" by X. Dong et al. Comp and Math Methods in Med. vol. 2013, Issue 1, Nov. 20, 2013 (Year: 2013).*
(Continued)

Primary Examiner — Jason M Ip
(74) Attorney, Agent, or Firm — KDW FIRM PLLC

(57) ABSTRACT

Systems and related methods for stationary digital chest tomosynthesis (s-DCT) imaging are disclosed. In some aspects, systems include a stationary x-ray source array with an array of x-ray pixels configured to generate x-ray beams at different viewing angles relative to a subject to be imaged that is stationary, a stationary area x-ray detector configured to record x-ray projection images of the subject, a physiological gating apparatus for monitoring at least one physi-
(Continued)

ological signal of the subject and defining a physiological phase and a time window based on the at least one physiological signal, and a computing platform configured to activate the x-ray pixels based on the physiological phase and the time window and upon receipt of the at least one physiological signal from the physiological gating apparatus in order to synchronize x-ray exposure with the at least one physiological signal of the subject.

18 Claims, 10 Drawing Sheets

Related U.S. Application Data

(60) Provisional application No. 62/066,091, filed on Oct. 20, 2014.

(51) Int. Cl.
*A61B 6/06* (2006.01)
*A61B 6/40* (2024.01)
*A61B 6/50* (2024.01)

(52) U.S. Cl.
CPC .............. *A61B 6/488* (2013.01); *A61B 6/502* (2013.01); *A61B 6/5205* (2013.01); *A61B 6/541* (2013.01); *A61B 6/4085* (2013.01)

(56) References Cited

U.S. PATENT DOCUMENTS

| | | |
|---|---|---|
| 3,733,484 A | 5/1973 | Bayard |
| 3,753,020 A | 8/1973 | Zingaro |
| 3,783,288 A | 1/1974 | Barbour et al. |
| 3,921,022 A | 11/1975 | Levine |
| 3,932,756 A | 1/1976 | Cowell et al. |
| 4,012,656 A | 3/1977 | Norman et al. |
| 4,253,221 A | 3/1981 | Cochran, Jr. et al. |
| 4,289,969 A | 9/1981 | Cooperstein et al. |
| 4,712,226 A | 12/1987 | Horbaschek |
| 4,728,576 A | 3/1988 | Gillberg-LaForce et al. |
| 4,809,308 A | 2/1989 | Adams et al. |
| 4,926,452 A | 5/1990 | Baker et al. |
| 4,958,365 A | 9/1990 | Sohval et al. |
| 5,129,850 A | 7/1992 | Kane et al. |
| 5,138,237 A | 8/1992 | Kane et al. |
| 5,241,578 A | 8/1993 | MacMahon |
| 5,245,648 A | 9/1993 | Kinney et al. |
| 5,305,363 A | 4/1994 | Burke et al. |
| 5,317,618 A | 5/1994 | Nakahara et al. |
| 5,371,778 A | 12/1994 | Yanof et al. |
| 5,377,249 A | 12/1994 | Wiesent et al. |
| 5,412,703 A | 5/1995 | Goodenough et al. |
| 5,424,054 A | 6/1995 | Bethune et al. |
| 5,557,105 A | 9/1996 | Honjo et al. |
| 5,578,821 A | 11/1996 | Meisberger et al. |
| 5,594,770 A | 1/1997 | Bowles et al. |
| 5,616,368 A | 4/1997 | Jin et al. |
| 5,623,180 A | 4/1997 | Jin et al. |
| 5,637,950 A | 6/1997 | Jin et al. |
| 5,648,699 A | 7/1997 | Jin et al. |
| 5,692,028 A | 11/1997 | Geus et al. |
| 5,726,524 A | 3/1998 | Debe |
| 5,745,437 A | 4/1998 | Wachter et al. |
| 5,764,683 A | 6/1998 | Swift et al. |
| 5,773,834 A | 6/1998 | Yamamoto et al. |
| 5,773,921 A | 6/1998 | Keesmann et al. |
| 5,786,895 A | 7/1998 | Mitchell et al. |
| 5,828,722 A | 10/1998 | Ploetz et al. |
| 5,834,783 A | 11/1998 | Muraki et al. |
| 5,844,963 A | 12/1998 | Koller et al. |
| 5,910,974 A | 6/1999 | Kuhn et al. |
| 5,973,444 A | 10/1999 | Xu et al. |
| RE36,415 E | 11/1999 | McKenna |
| 5,976,444 A | 11/1999 | Pearson et al. |
| 6,019,656 A | 2/2000 | Park et al. |
| 6,028,911 A | 2/2000 | Kawahara |
| 6,057,637 A | 5/2000 | Zetti et al. |
| 6,087,765 A | 7/2000 | Coll et al. |
| 6,097,138 A | 8/2000 | Nakamoto |
| 6,097,788 A | 8/2000 | Berenstein et al. |
| 6,125,167 A | 9/2000 | Morgan |
| 6,165,181 A | 12/2000 | Heilbrun et al. |
| 6,178,226 B1 | 1/2001 | Hell et al. |
| 6,192,104 B1 | 2/2001 | Adams et al. |
| 6,250,984 B1 | 6/2001 | Jin et al. |
| 6,259,765 B1 | 7/2001 | Baptist |
| 6,271,923 B1 | 8/2001 | Hill |
| 6,277,318 B1 | 8/2001 | Bower et al. |
| 6,280,697 B1 | 8/2001 | Zhou et al. |
| 6,297,592 B1 | 10/2001 | Goren et al. |
| 6,333,968 B1 | 12/2001 | Whitlock et al. |
| 6,334,939 B1 | 1/2002 | Zhou et al. |
| 6,385,292 B1 | 5/2002 | Dunham et al. |
| 6,440,761 B1 | 8/2002 | Choi |
| 6,445,122 B1 | 9/2002 | Chuang et al. |
| 6,447,163 B1 | 9/2002 | Bani-Hashemi et al. |
| 6,456,691 B2 | 9/2002 | Takahashi et al. |
| 6,459,767 B1 | 10/2002 | Boyer et al. |
| 6,470,068 B2 | 10/2002 | Cheng |
| 6,498,349 B1 | 12/2002 | Thomas et al. |
| 6,510,195 B1 | 1/2003 | Chappo et al. |
| 6,545,396 B1 | 4/2003 | Ohki et al. |
| 6,553,096 B1 | 4/2003 | Zhou et al. |
| RE38,223 E | 8/2003 | Keesmann et al. |
| 6,621,887 B2 | 9/2003 | Albagli et al. |
| 6,630,772 B1 | 10/2003 | Bower et al. |
| 6,650,730 B2 | 11/2003 | Bogatu et al. |
| 6,672,926 B2 | 1/2004 | Liu et al. |
| 6,674,837 B1 | 1/2004 | Taskar et al. |
| 6,753,931 B2 | 6/2004 | Kane et al. |
| 6,760,407 B2 | 7/2004 | Price et al. |
| RE38,561 E | 8/2004 | Keesmann et al. |
| 6,787,122 B2 | 9/2004 | Zhou |
| 6,850,595 B2 | 2/2005 | Zhou et al. |
| 6,852,973 B2 | 2/2005 | Suzuki et al. |
| 6,876,724 B2 | 4/2005 | Zhou et al. |
| 6,885,022 B2 | 4/2005 | Yaniv et al. |
| 6,914,959 B2 | 7/2005 | Bailey et al. |
| 6,917,664 B2 | 7/2005 | Chappo et al. |
| 6,940,943 B2 | 9/2005 | Hermann et al. |
| 6,949,877 B2 | 9/2005 | Sun et al. |
| 6,965,199 B2 | 11/2005 | Stoner et al. |
| 6,980,627 B2 | 12/2005 | Qiu et al. |
| 6,999,554 B2 | 2/2006 | Mertelmeier |
| 7,027,558 B2 | 4/2006 | Ghelmansarai et al. |
| 7,046,757 B1 | 5/2006 | Bani-Hashemi et al. |
| 7,082,182 B2 | 7/2006 | Zhou et al. |
| 7,085,351 B2 | 8/2006 | Lu et al. |
| 7,103,137 B2 | 9/2006 | Seppi et al. |
| 7,129,513 B2 | 10/2006 | Zhou et al. |
| 7,147,894 B2 | 12/2006 | Zhou et al. |
| 7,152,432 B2 | 12/2006 | Wanner et al. |
| 7,187,756 B2 | 3/2007 | Gohno et al. |
| 7,192,031 B2 | 3/2007 | Dunham et al. |
| 7,227,924 B2 | 6/2007 | Zhou et al. |
| 7,245,692 B2 | 7/2007 | Lu et al. |
| 7,245,694 B2 | 7/2007 | Jing et al. |
| 7,252,749 B2 | 8/2007 | Zhou et al. |
| 7,294,248 B2 | 11/2007 | Gao |
| 7,330,529 B2 | 2/2008 | Kautzer et al. |
| 7,359,484 B2 | 4/2008 | Qiu et al. |
| 7,428,298 B2 | 9/2008 | Bard et al. |
| 7,440,603 B2 | 10/2008 | Eberhard et al. |
| 7,581,884 B1 | 9/2009 | Barnes et al. |
| 7,639,775 B2 | 12/2009 | DeMan et al. |
| 7,656,999 B2 | 2/2010 | Hui et al. |
| 7,736,055 B2 | 6/2010 | Hornig |
| 7,741,624 B1 | 6/2010 | Sahadevan |
| 7,751,528 B2 | 7/2010 | Zhou et al. |
| 7,835,492 B1 | 11/2010 | Sahadevan |
| 7,887,689 B2 | 2/2011 | Zhou et al. |
| 7,902,530 B1 | 3/2011 | Sahadevan |

(56) References Cited

U.S. PATENT DOCUMENTS

| | | | |
|---|---|---|---|
| 7,940,887 B2 | 5/2011 | Shibata et al. | |
| 8,576,988 B2 | 11/2013 | Lewalter et al. | |
| 8,670,521 B2 | 3/2014 | Bothorel et al. | |
| 8,821,015 B2 | 9/2014 | Stagnitto et al. | |
| 8,873,712 B2 | 10/2014 | Wang et al. | |
| 8,983,024 B2* | 3/2015 | Zhang | A61B 6/466 378/22 |
| 9,036,775 B2 | 5/2015 | Yoshikawa et al. | |
| 9,299,190 B2 | 3/2016 | Koivisto et al. | |
| 9,438,897 B2 | 9/2016 | Barreto et al. | |
| 9,782,136 B2 | 10/2017 | Zhou et al. | |
| 9,907,520 B2 | 3/2018 | Zhou et al. | |
| 10,539,708 B2 | 1/2020 | Zhou et al. | |
| 10,835,199 B2 | 11/2020 | Chtcheprov | |
| 10,980,494 B2 | 4/2021 | Lu et al. | |
| 2002/0041655 A1 | 4/2002 | Mitschke | |
| 2002/0080921 A1 | 6/2002 | Smith et al. | |
| 2002/0085674 A1 | 7/2002 | Price et al. | |
| 2003/0002627 A1 | 1/2003 | Espinosa et al. | |
| 2003/0002628 A1 | 1/2003 | Wilson et al. | |
| 2003/0102222 A1 | 6/2003 | Zhou et al. | |
| 2003/0128801 A1* | 7/2003 | Eisenberg | A61B 6/466 378/19 |
| 2004/0036402 A1 | 2/2004 | Keesmann et al. | |
| 2004/0108298 A1 | 6/2004 | Gao | |
| 2004/0213378 A1 | 10/2004 | Zhou et al. | |
| 2004/0240616 A1 | 12/2004 | Qiu et al. | |
| 2004/0256975 A1 | 12/2004 | Gao et al. | |
| 2005/0133372 A1 | 6/2005 | Zhou et al. | |
| 2005/0226371 A1 | 10/2005 | Kautzer et al. | |
| 2005/0226375 A1 | 10/2005 | Eberhard et al. | |
| 2005/0281379 A1 | 12/2005 | Qiu et al. | |
| 2005/0285541 A1 | 12/2005 | LeChevalier | |
| 2006/0067473 A1 | 3/2006 | Eberhard et al. | |
| 2007/0009081 A1 | 1/2007 | Zhou et al. | |
| 2007/0009088 A1 | 1/2007 | Edic et al. | |
| 2008/0219567 A1 | 9/2008 | Claus et al. | |
| 2008/0240343 A1 | 10/2008 | Jabri et al. | |
| 2009/0022264 A1 | 1/2009 | Zhou et al. | |
| 2009/0041201 A1 | 2/2009 | Wang et al. | |
| 2009/0116617 A1 | 5/2009 | Mastronardi et al. | |
| 2010/0034450 A1 | 2/2010 | Mertelmeier | |
| 2010/0063410 A1 | 3/2010 | Avila | |
| 2013/0004042 A1* | 1/2013 | Yang | A61B 6/032 382/131 |
| 2013/0294666 A1 | 11/2013 | Bultema | |
| 2014/0185751 A1* | 7/2014 | De Man | H05G 1/28 378/165 |
| 2014/0221824 A1 | 8/2014 | Rai et al. | |
| 2015/0230768 A1 | 8/2015 | Belei | |
| 2015/0359504 A1 | 12/2015 | Zhou et al. | |
| 2016/0106316 A1 | 4/2016 | Lu et al. | |
| 2016/0193482 A1 | 7/2016 | Fahrig et al. | |
| 2016/0317107 A1 | 11/2016 | Zhou et al. | |
| 2016/0325835 A1 | 11/2016 | Abuelsaad et al. | |
| 2017/0085867 A1 | 3/2017 | Baran et al. | |
| 2017/0219498 A1 | 8/2017 | Chtcheprov | |
| 2017/0329037 A1 | 11/2017 | Zhou et al. | |

FOREIGN PATENT DOCUMENTS

| | | |
|---|---|---|
| CN | 1316279 | 10/2001 |
| CN | 2462856 Y | 12/2001 |
| CN | 1589744 A | 3/2005 |
| CN | 1672637 A | 9/2005 |
| CN | 1768707 A | 5/2006 |
| CN | 1919372 A | 2/2007 |
| CN | 101641589 A | 2/2010 |
| CN | 101842052 | 9/2010 |
| CN | 101842052 A | 9/2010 |
| CN | 101960333 A | 1/2011 |
| CN | ZL200680013859.X | 1/2011 |
| CN | 102551783 A | 7/2012 |
| CN | 102579061 A | 7/2012 |
| CN | 102870189 A | 1/2013 |
| CN | 103578082 A | 2/2014 |
| CN | 105411620 A | 3/2016 |
| CN | 105615911 B | 7/2021 |
| DE | 19700992 | 7/1998 |
| DE | 10164315 A1 | 8/2002 |
| DE | 10164318 A1 | 8/2002 |
| EP | 0 268 488 | 5/1988 |
| EP | 0 648 468 A1 | 4/1995 |
| EP | 1 050 272 A1 | 11/2000 |
| GB | 679617 | 9/1952 |
| JP | 53103392 | 9/1978 |
| JP | S54027793 | 2/1979 |
| JP | 57162431 A2 | 10/1982 |
| JP | 60254615 A2 | 12/1985 |
| JP | S61-142644 | 6/1986 |
| JP | 06163381 A2 | 6/1994 |
| JP | 08264139 | 10/1996 |
| JP | 09180894 | 7/1997 |
| JP | 11-111158 | 4/1999 |
| JP | H11-116218 | 4/1999 |
| JP | 11-260244 | 9/1999 |
| JP | 2000-208028 | 7/2000 |
| JP | 2000251826 A2 | 9/2000 |
| JP | 2001-048509 | 2/2001 |
| JP | 2001190550 | 7/2001 |
| JP | 2001250496 | 9/2001 |
| JP | 2003100242 A | 4/2003 |
| TW | 00319886 | 11/1997 |
| TW | 0527624 B | 4/2003 |
| TW | 0529050 B | 4/2003 |
| WO | WO 98/57349 | 12/1998 |
| WO | WO 00/51936 A3 | 9/2000 |
| WO | WO 01/58525 | 8/2001 |
| WO | WO 02/03413 | 1/2002 |
| WO | WO 02/31857 | 4/2002 |
| WO | WO 03/012816 A2 | 2/2003 |
| WO | WO 2004/061477 | 7/2004 |
| WO | WO 2005/079246 | 1/2005 |
| WO | WO 2006/116365 A2 | 11/2006 |
| WO | WO 2009/067394 A2 | 5/2009 |
| WO | WO 2013/080111 A1 | 6/2013 |

OTHER PUBLICATIONS

Bentley, M.D. et al., "The Use of Microcomputed Tomography to Study Microvasculature in Small Rodents", Am. J Physiol Regulatory Integrative Comp Physiol, 282, pp. R1267-1279, 2002.

Bonard, et al., "Field emission from single-wall carbon nanotube films," Appl. Phys. Lett., vol. 73, No. 7, pp. 918-920 (Aug. 17, 1998).

Bower, et al., "Synthesis and structure of pristine and alkali-metal-intercalated single-walled carbon nanotubes," Appl. Phys., A 67, pp. 47-52 (1998).

Bower, C. et al., "Fabrication and Field Emission Properties of Carbon Nanotube Cathodes", Mat. Res. Soc. Symp. Proc., vol. 593, pp. 215-220, 2000.

Brock et al., "Hadamard Transform Time-of-Flight Mass Spectrometry," Analytical Chemistry, vol. 70. No. 18, Sep. 15, 1998.

Brodie, et al., "Vacuum Microelectronics," Advance in Electronics and Electron Physics, edited by P.W. Hawkes, vol. 83, pp. 1-106 (1992).

Bushong, S.C., "Radiologic Science for Technologist," Physics, Biology, and Protection, 6th Edition, Mosby, Inc., 1997 (pp. 107-125) (excerpt relating to focusing and thermionic emission).

A.M. Cassell, et al., "Large Scale CVD Synthesis of Single-Walled Carbon Nanotubes," J. Phys. Chem., B 103, pp. 6484-6492 (Jul. 20, 1999).

Charbonnier et al., "Resolution of Field-Emmision X-Ray Sources," Radiology, vol. 117: pp. 165-172 (Oct. 1975).

Cheng et al., "Dynamic radiography using a carbon-nanotube-based field emmision x-ray source," Review of Scientific Instruments, vol. 75, No. 10: pp. 3264-3267 (Oct. 2004).

De Heer, et al., "A Carbon Nanotube Field-Emission Electron Source," Science, vol. 270, pp. 1179-1180 (Nov. 17, 1995).

(56) References Cited

OTHER PUBLICATIONS

Dobbins et al., "Digital X-ray tomosynthesis: current state of the art and clinical potential," Phys. Med. Biol., vol. 48, p. 65-106 (2003).
Feldkamp L.A. et al., "Practical Cone-Beam Algorithm", J. Opt. Soc. Am., 1(a):612-619, 1984.
Gao et al., "Fabrication and Electron Field Emmision Properties of Carbon Nanotube Films by Electrophoretic Deposition," Advanced Materials, vol. 13, No. 23 (2001) pp. 1770-1773.
Gauntt, D.M., et al., "An automatic and accurate x-ray tube focal spot/grid alignment system for mobile radiography: System description and alignment accuracy," Med. Phys. 37:12, pp. 6402-6410 (2010).
Geis, et al., "Diamond emitters fabrication and theory," J. Vac. Sci. Technol. B, vol. 14, No. 3, pp. 2060-2067, May/Jun. 1996.
Groenhuis, et al., "Computerized tomosynthesis of dental tissues," Oral Surg Oral Med Oral Pathol, 1983. 56: p. 206-214.
Hallenbeck, "Clinical Evaluation of the 350-kV Chest Radiography System," Radiology, vol. 117: pp. 1-4 (1974).
Hu, J. et al., "Chemistry and Physics in One Dimension: Synthesis and Properties of Nanowires and Nanotubes", Accounts of Chemical Research, vol. 32, pp. 435-445, 1999.
C. Journet, et al., "Large-scale production of single-walled carbon nanotubes by the electric-arc technique," Nature, vol. 388, pp. 756-760 (Aug. 21, 1997).
Kumar, et al., "Diamond-based field emission flat panel displays," Solid State Technology, vol. 38, pp. 71-74 (May 1995).
Liang Li, et al., "X-ray digital intra-oral tomosynthesis for quasi-three-dimensional imaging: system, reconstruction algorithm, and experiments," Optical Engineering, 2013. 52(1): p. 013201.
Miao, H., et al., "A phantom-based calibration method for digital x-ray tomosynthesis," J. X-Ray Scl. Technol. 20, pp. 17-29 (2012).
Moore et al., "Three-Dimensional X-Ray Laminography as a Tool for Detection and Characterization of BGA Package Defects", IEEE Transactions on Components and Packaging Technologies. vol. 25, No. 2, Jun. 2002.
Okano, et al., "Electron emission from nitrogen-doped pyramidal-shape diamond and its battery operation," Appl. Phys. Lett., vol. 70, No. 16, pp. 2201-2203 (Apr. 21, 1997).
Okano, et al., "Fabrication of a diamond field emitter array," Appl. Phys. Lett., vol. 64, No. 20, pp. 2742-2744 (May 16, 1994).
Okazaki, et al., "A New Emission Spectrum of Au2 in the Gas Evaporation Technique: 761-809 nm," Jpn. J. Appl. Phys., vol. 37, Pt. 1, No. 1, pp. 349-350 (Jan. 1998).
Qian, X., et al., "High resolution stationary digital breast tomosynthesis using distributed carbon nanotube x-ray source array," Med. Phys. 39:4, pp. 2090-2099 (2012).
Resat et al., "Microbeam developments and applications: a low linear energy transfer perspective," Cancer and Metastasis Reviews 23: p. 323-331 (2004).
Ribbing et al., "Diamond membrane based sructures for miniature X-ray sources," Diamond and Related Materials, vol. 11: pp. 1-7 (2002).
Rinzler, et al., "Unraveling Nanotubes: Field Emission from an Atomic Wire," Science, vol. 269, pp. 1550-1553 (Sep. 15, 1995).
Saito, Y. et al., "Field Emission Patterns from Single-Walled Carbon Nanotubes", Jpn. J. Appl. Phys., vol. 36, pp. L1340-L1342, Part 2, No. 10A, Oct. 1, 1997.
Saito, Y. et al., "Cathode Ray Tube Lighting Elements with Carbon Nanotube Field Emitters", Jpn. J. Appl. Phys., vol. 37, pp. L346-L348, Part 2, No. 3B, Mar. 15, 1998.
Shan, J., et al., "Stationary chest tomosynthesis using a CNT x-ray source array," Proc. SPIE Medical Imaging, vol. 8668, pp. 86680E 1-12 (2013).
Slatkin, D et al., Proc. Natl. Acac. Sci. USA, vol. 92, pp. 8783-8787, 1995.
Sloane, "Multiplexing Methods in Spectroscopy," Mathematics Magazine, vol. 52, No. 2 (Mar. 1979), 71-80.
Sugie et al., "Carbon nanotubes as electron source in an x-ray tube," Applied Physics Letters, vol. 78, No. 17: pp. 2578-2580 (2001).

Svahn, T.M., et al., "Breast tomosynthesis and digital mammography: a comparison of diagnostic accuracy," Br. J. Radiol., 85, pp. e1074-e1082 (2012).
Tang, et al., "Electronic Structures of Single-Walled Carbon Nanotubes Determined by NMR," Science, vol. 288, pp. 492-494 (Apr. 21, 2000).
Thess, et al., "Crystalline Ropes of Metallic Carbon Nanotubes," Science, vol. 273, pp. 483-487 (Jul. 26, 1996).
Tingberg, "X-ray tomosynthesis: a review of its use for breast and chest imaging," Radiat. Prot. Dosimetry, vol. 139, No. 1-3, pp. 100-107 (2010).
Traedo, "A Thousand Points of Light: The Hadamard Transform in Chemical Analysis and Instrumentation," Analytical Chemistry. vol. 61, No. 11, Jun. 1, 1989.
Vogel et al., "A New Method of Multiplanar Emission Tomography Using a Seven Pinhole Collimator and an Anger Scintillation Camera," Jour. Nuclear Medicine, vol. 19, No. 6, pp. 648-654, 1978.
Wang, et al., "Field emission from nanotube bundle emitters at low fields," Appl. Phys. Leff., vol. 70, No. 24, pp. 3308-3310 (Jun. 16, 1997).
Wang, et al., "A nanotube-based field-emission flat panel display," Appl. Phys. Lett., vol. 72, No. 2, pp. 2912-2913 (Jun. 1, 1998).
Webber, et al., "Comparison of film, direct digital, and tuned-aperture computed tomography images to identify the location of crestal defects around endosseous titanium implants," Oral Surg Oral Med Oral Pathol Oral Radiol Endod 1996. 81: p. 480-490.
Webber, et al., "Hand-held three-dimensional dental x-ray system: technical description and preliminary results," Dentomaxillofacial Radiology, 2002. 31: p. 240.
Weinstein et al., "Data Transmission by Frequency-Division Multiplexing Using the Discrete Fourier Transform," IEEE Trans. on Commun. Tech., vol. Com-19, No. 5, pp. 628-634, Oct. 1971.
Yagishita, et al., "Effects of Cleavage on Local Cross-Sectional Stress Distribution in Trench Isolation Structure," Jpn. J. Appl. Phys., vol. 36, pp. 1335-1340 (Mar. 1997).
Yue et al., "Generation of continuous and pulsed diagnostic imaging x-ray radiation using a carbon nontube based field emission cathode," Applied Physics Letters, vol. 81, No. 2: pp. 355-357 (F) Jul. 8, 2002.
Zhang et al., "Multiplexing radiography using a carbon nanotube based x-ray source," Applied Physics Letters, vol. 89, Aug. 2006.
Zhang et al., "Stationary scanning x-ray source based on carbon nanotube field emitters," Applied Physics Letters, vol. 86, 2005.
Zhou et al., "Materials Science of Carbon Nanotubes: Fabrication, Integration, and Properties of Macroscopic Structures of Carbon Nanotubes", Acc. Chem. Res., vol. 35, pp. 1045-1053, 2002.
Zhu, et al., "Large Current Density from Carbon Nanotube Filed Emitters," Appl. Phys. Lett., American Institute of Physics, vol. 75, No. 6, Aug. 9, 1999, pp. 873-875.
Zhu, et al., "Low-Field Electron Emission from Undoped Nanostructured Diamond," Science, vol. 282, 1471-1473 (Nov. 20, 1998).
Ziegler, et al., "Digital tomosynthesis—experiences with a new imaging device for the dental field," Clin Oral Invest, 2003. 7: p. 41-45.
International Search Report and Written Opinion for PCT Application No. PCT/US08/70477 dated Oct. 1, 2008.
Non-Final Office Action for U.S. Appl. No. 12/176,056 dated Sep. 2, 2009.
First Office Action from Chinese Patent Office for Chinese Patent Application Serial No. 200680013859.X dated Sep. 25, 2009.
Notice of Allowance for U.S. Appl. No. 12/176,056 dated Apr. 2, 2010.
Second Office Action corresponding to Chinese Patent Application No. 200680013859 dated Apr. 30, 2010.
First Office Action for CN Appl. No. 200880107680.X dated Apr. 7, 2011.
Chinese Office Action for Application No. 200880107680.X dated Jan. 14, 2013.
Chinese Notice of Grant for Application No. 200880107680.X dated Aug. 6, 2013.
Non-Final Office Action for U.S. Appl. No. 14/741,041 dated Aug. 18, 2016.

(56) References Cited

OTHER PUBLICATIONS

Non-Final Office Action for U.S. Appl. No. 15/205,787 dated May 19, 2017.
Final Office Action for U.S. Appl. No. 14/741,041 dated Apr. 26, 2017.
Notice of Allowance for U.S. Appl. No. 14/741,041 dated Jul. 17, 2017.
German Office Action for German Application No. 112008001902 dated Sep. 15, 2017.
Final Office Action for U.S. Appl. No. 15/205,787 dated Oct. 25, 2017.
Notice of Allowance for U.S. Appl. No. 15/205,787 dated Jan. 3, 2018.
Non-Final Office Action for U.S. Appl. No. 14/886,842 dated Jun. 10, 2019.
Non-Final Office Action for U.S. Appl. No. 15/421,869 dated Aug. 22, 2019.
Notice of Allowance for U.S. Appl. No. 15/587,052 dated Sep. 13, 2019.
Final Office Action for U.S. Appl. No. 14/886,842 dated Oct. 23, 2019,.
Chinese Office Action for Application No. 201510916422.8 dated Nov. 21, 2019.
Chinese Office Action for Application No. 201510450909.1 dated Feb. 3, 2020.
Final Office Action for U.S. Appl. No. 15/421,869 dated Feb. 5, 2020.
Chinese Office Action for Application No. 201510450909.1 dated Jun. 5, 2020.
Non-Final Office Action for U.S. Appl. No. 14/886,842 dated Jul. 29, 2020.
Chinese Office Action for Application No. 201510916422.8 dated Aug. 13, 2020.
Notice of Allowance for U.S. Appl. No. 15/421,869 dated Sep. 2, 2020.
Corrected Notice of Allowance for U.S. Appl. No. 15/421,869 dated Oct. 26, 2020.
Notice of Allowance and Interview Summary for U.S. Appl. No. 14/886,842 dated Nov. 20, 2020.
Chinese Office Action for Application No. 201510916422.8 dated Jan. 12, 2021.
Chinese Office Action for Application No. 2015104509091 dated Nov. 30, 2022.
Chinese Office Action for Application No. 20211078315 dated Sep. 21, 2023.

\* cited by examiner

SYSTEMS AND RELATED METHODS FOR STATIONARY DIGITAL CHEST TOMOSYNTHESIS (S-DCT) IMAGING

CROSS-REFERENCE TO RELATED APPLICATIONS

This patent application is a continuation of and claims priority to U.S. patent application Ser. No. 14/886,842, filed Oct. 19, 2015, which claims priority to U.S. Provisional Application Ser. No. 62/066,091, filed Oct. 20, 2014, the disclosures of which are incorporated by reference herein in their entireties.

GOVERNMENT INTEREST

This invention was made with government support under Grant No. U54CA151652 awarded by NIH. The government has certain rights in the invention.

TECHNICAL FIELD

The subject matter described herein relates to x-ray radiography and tomography. More specifically, the subject matter disclosed herein relates to systems and related methods for stationary digital chest tomosynthesis (s-DCT) imaging.

BACKGROUND

Lung cancer continues to be the leading cause of cancer deaths in the world. Over 200,000 new cases of lung cancer are identified in the United States per year, and the number of deaths from lung cancer exceeds the total deaths from breast, prostate, and colon cancer combined. In spite of decades of research on diagnosis and therapy, survival rates remain poor. Possible screening tests for lung cancer include chest x-ray radiograph (CXR), and computed tomography (CT). CXR imaging is well known to perform poorly in screening and identification of small cancers due to small lesion size and poor conspicuity. CT imaging is the current gold standard for imaging pulmonary lesions since it can eliminate any overlapping anatomical structures and reveal hidden lung nodules. However, CT imaging involves both high costs and high radiation doses, which can lead to radiation induced cancer. Thus, CT imaging of lung cancer is not recommended for the general population.

Digital tomosynthesis is a three-dimensional (3D) imaging technique that provides reconstruction slice images from a limited-angle series of projection images. Digital tomosynthesis improves the visibility of anatomical structures by reducing visual clutter from overlying normal anatomy. Some examples of current clinical tomosynthesis applications include chest, abdominal, musculoskeletal, and breast imaging. Digital chest tomosynthesis (DCT) imaging improves the visibility of anatomical structures such as the pulmonary vessels, bronchial walls, small airways, vascular trees, and bronchiectasis when compared to CXR imaging. DCT imaging displays the lungs in the coronal plane with contiguous slices and gives a better overview of the bronchial tree when compared to traditional axial CT imaging. DCT imaging has better resolution than CT imaging in a plane of the image because it yields coronal images and utilizes a higher resolution detector compared to CT imaging, whereas the spatial resolution of CT imaging is limited for the most part by a z-axis resolution of its detectors. By reducing visual clutter from overlying normal anatomy, DCT imaging also enhances detection of small lung nodules. Equally significant, the radiation dose used in DCT imaging is approximately between 10-40 times lower than CT imaging and its cost is only a fraction (i.e., about one tenth) of CT imaging.

There are several commercial digital tomosynthesis systems including, for example, VOLUMERAD® and RADSPEED® for chest imaging, SELENIA® DIMENSION® and Siemens MAMMOMAT INSPIRATION® for breast imaging. The design of existing commercial tomosynthesis systems are all similar, in which an x-ray tube with a single x-ray generating focal spot is used to collect the projection images by moving the x-ray source over approximately a 10-50 degree arc angle related to a subject being imaged. Due to gantry rotation and mechanical instability, effective focal spot size during image acquisition is larger than the static value which degrades the image resolution. Accordingly it is desirable to provide a digital tomosynthesis image system that does not require mechanical motion of the x-ray source.

More importantly, mechanical motion of a heavy x-ray source gantry over a linear or arc trajectory requires acceleration and deceleration of the gantry. The instability associated with acceleration limits a maximum speed the gantry can move, thus intrinsically limiting a speed of tomosynthesis image acquisition. Typically, a minimum scan time for existing moving gantry chest tomosynthesis systems is five seconds or more; the typical respiration period for adults is three to five seconds, and one to three seconds for children. Thus, conventional tomosynthesis imaging systems generally result in very poor image quality due to physiological movement of the patient. Existing moving gantry chest tomosynthesis systems require a breath-hold for imaging, and generally are not suitable for pediatric imaging. For many lung disease patients and children, holding their breath for five seconds or more can be difficult. Accordingly, it is desirable to provide systems and related methods for stationary digital tomosynthesis imaging that render patent motion insignificant.

SUMMARY

Systems and related methods for stationary digital chest tomosynthesis (s-DCT) imaging are disclosed. In some aspects, the systems and related methods enable s-DCT imaging that drastically reduces motion blurring caused by respiratory and cardiovascular motion, which systems and related methods can, for example, be used for applications other than chest tomography imaging.

In some aspects, a system can comprise a stationary x-ray source array comprising an array of spatially distributed x-ray pixels configured to generate x-ray beams at different viewing angles relative to a subject to be imaged that is stationary, a stationary area x-ray detector positioned substantially parallel to a plane of the x-ray source array and configured to record x-ray projection images of the subject from the different viewing angles for tomosynthesis reconstruction, a physiological gating apparatus for monitoring at least one physiological signal of the subject, the physiological gating apparatus defining a physiological phase and a time window based on the at least one physiological signal during which the x-ray projection images of the subject from the different viewing angles are acquirable, and a computing platform comprising at least one hardware processor and a memory, the computing platform being configured to activate the x-ray pixels based on the physiological phase and the time window and upon receipt of the at least one physiological signal from the physiological gating apparatus in order to synchronize x-ray exposure with the at least one physiological signal of the subject.

In some aspects, a method can comprise providing a stationary x-ray source array comprising an array of spatially distributed x-ray pixels configured to generate x-ray beams at different viewing angles relative to a subject to be imaged that is stationary, and providing a stationary area x-ray detector positioned substantially parallel to a plane of the x-ray source array and configured to record x-ray projection images of the subject from the different viewing angles for tomosynthesis reconstruction, monitoring, by a physiological gating apparatus, at least one physiological signal of the subject, the physiological gating apparatus defining a physiological phase and a time window based on the at least one physiological signal during which the x-ray projection images of the subject from the different viewing angles are acquirable, activating, by the computing platform, the x-ray pixels upon receiving the at least one physiological signal in order to synchronize x-ray exposure with the at least one physiological signal of the subject, and recording x-ray projection images of the subject from the different viewing angles.

In some aspects, a method for producing fast tomography images of a human chest or torso can comprise providing an x-ray source array configured to generate cone-beam x-ray radiation from an array of spatially distributed x-ray focal spots, collimating the x-ray radiation from each of the x-ray focal spots of the x-ray source array to a region of interest in an area x-ray detector, detecting and collecting projection images of an object with a primary beam sampling apparatus placed in between the x-ray source array and the area x-ray detector, estimating and subtracting a scatter signal profile of the object from the projection images, and reconstructing tomography images based on projection images with a reduced scatter signal.

In some aspects, a method for producing one or more images of an object using at least one of monochromatic and quasi-monochromatic x-ray beams, the method can comprise providing field emission x-ray sources with spatially distributed focal spots with respect to an object to be imaged, irradiating the object with at least one of monochromatic and quasi-monochromatic x-ray beams produced by the x-ray sources to generate projection images of the object, detecting the projection images of the object, and reconstructing one or more displayable images of the object based on the projection images of the object.

The subject matter disclosed herein can be implemented in software in combination with hardware and/or firmware. For example, the subject matter described herein can be implemented in software executed by a processor. In one exemplary implementation, the subject matter described herein can be implemented using a computer readable medium having stored thereon computer executable instructions that when executed by a processor of a computer control the computer to perform steps. Exemplary computer readable mediums suitable for implementing the subject matter described herein include non-transitory devices, such as disk memory devices, chip memory devices, programmable logic devices, and application specific integrated circuits. In addition, a computer readable medium that implements the subject matter described herein can be located on a single device or computing platform or can be distributed across multiple devices or computing platforms.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described herein below.

BRIEF DESCRIPTION OF THE DRAWINGS

Features and advantages of the present subject matter will be more readily understood from the following detailed description which should be read in conjunction with the accompanying drawings that are given merely by way of explanatory and non-limiting example, and in which.

DETAILED DESCRIPTION

Figure 1:
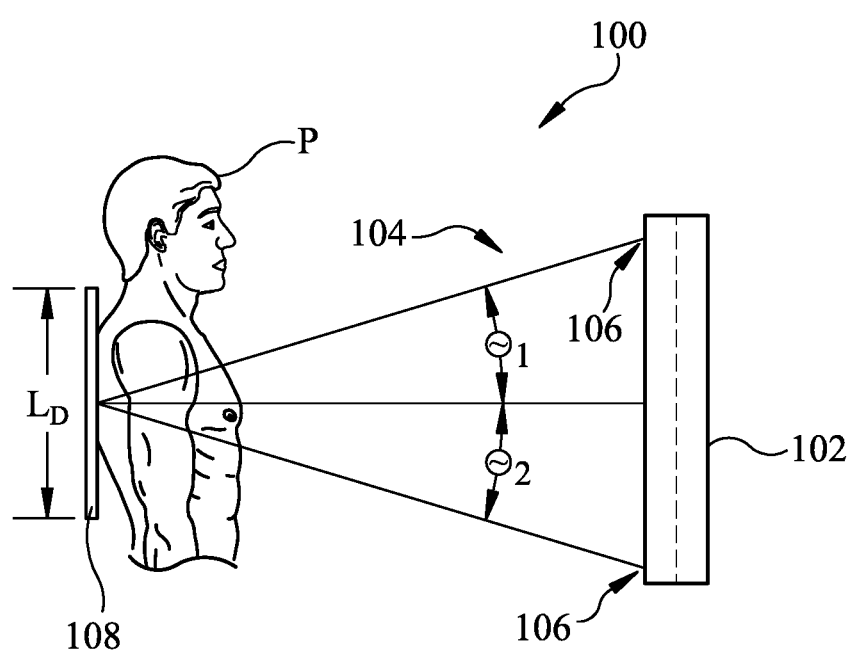
FIG. 1 is a schematic diagram illustrating an exemplary stationary digital chest tomosynthesis (s-DCT) system including a linear multiple beam x-ray source array according to some aspects of the present subject matter.

The present subject matter relates to systems and related methods for stationary digital chest tomosynthesis (s-DCT) imaging. In one aspect, the present subject matter provides s-DCT systems with an x-ray source array and/or an area x-ray detector that enables stationary tomosynthesis imaging, i.e., imaging without moving the x-ray source or detector. Notably, the systems and related methods for s-DCT imaging, as disclosed herein, can be used for additional applications such as, for example, dental, breast, abdominal imaging. For example, the systems and related methods disclosed herein may be used in stationary x-ray digital breast tomosynthesis imaging, as disclosed in U.S. Pat. No. 7,751,528 filed on Jul. 18, 2008, the disclosure of which is incorporated by reference herein as if set forth in its entirety.

Conventionally, digital chest tomosynthesis (DCT) systems comprise an x-ray detector and an object that each remain stationary, while an x-ray source mechanically moves along a linear trajectory and rotates to obtain different projection views of the object. In this manner, physical limits to acceleration and deceleration of the x-ray source limits scanning speed of such conventional DCT systems. For example, most existing DCT systems require approximately 10-15 seconds for a scan, during which period significant motion of the object (e.g., heart, lung, and body motion), as well as focal spot blurring, is likely to occur. Where any type of movement or focal spot blurring occurs during the scan, image resolution and quality of the projection images can be degraded.

By comparison, FIGS. 1-11 provide exemplary s-DCT systems and related methods which utilize an x-ray source array, such as for example a carbon nanotube (CNT) field emission x-ray source array, which contains individual x-ray focal spots arranged in one-dimensional or two-dimensional patterns. Such an x-ray source array enables rapid acquisition (an average scan time of approximately two to five seconds, with a scanning time of one second or less being possible with fast frame detectors) of all projection images needed for tomosynthesis reconstruction without mechanical motion of the x-ray source, an object (e.g., patient), or an x-ray detector. This limits the likelihood of significant motion of the patient occurring. In addition, individual x-ray generation at each focal spot can be physiologically gated to generate radiation during predetermined physiological phases only, such that projection images are acquired at a same phase point over several respiratory cycles and do not require breath-holding of a patient. This can significantly reduce or potentially eliminate any focal spot blur caused by physiological motion between different projection images. Accordingly, by eliminating the mechanical motion, the exemplary s-DCT systems and related methods disclosed herein can acquire tomography images with higher quality and resolution and in a shorter scanning time.

Moreover, the s-DCT systems and related methods disclosed herein provide a low dose imaging modality. This advantageously permits acquiring multiple images of a patient over a period of time for longitudinal monitoring of disease progress and/or therapeutic effect. Such capability is important for many diseases such as, for example, lung cancer and cystic fibrosis disease.

Furthermore, the s-DCT systems and related methods disclosed herein provide for fast and gated imaging capability, which enables multiple phase tomosynthesis imaging of regions of interest (ROI), such as, for example, lungs and hearts, during respiration and cardiac cycles. In this manner, temporal three-dimensional (3D) or four-dimensional (4D) dynamic images of lungs and hearts are obtainable at low doses, as compared to computed tomography (CT) imaging.

As used herein, the terms "patient", "human", "subject", and "object" are used generically and interchangeably to mean an entity that is being scanned by the s-DCT system, unless otherwise specified.

Referring now to FIG. 1, a schematic diagram of an exemplary s-DCT system, generally designated 100, is illustrated. In some aspects, s-DCT system 100 can be used exclusively for imaging a patient's chest, while in other aspects s-DCT system 100 can be adapted for imaging a patient's breasts, mouth, abdomen, etc. S-DCT system 100 can comprise an x-ray source array, generally designated 102, that can obtain faster scan speeds without the mechanical motion that is present in conventional DCT systems. For example, x-ray source array 102 can comprise a linear multiple beam x-ray source array containing multiple, individually programmable x-ray pixels arranged linearly. In other aspects, the x-ray source array can comprise multiple, individually programmable x-ray pixels arranged in an arc, a circumference of a circle or a polygon, a two dimensional matrix, etc. Regardless, x-ray pixels of x-ray source array 102 can be evenly spaced and/or angled for directing x-ray beams 104 towards a patient P. In some aspects, x-ray source array 102 can comprise between 3 and 90 pixels. In some aspects, patient P can be irradiated with at least one of monochromatic and/or quasi-monochromatic x-ray beams produced by x-ray sources.

Each pixel can comprise a cathode (e.g. a CNT field emission cathode, thermionic cathode, or photocathode) (see 210, FIG. 2A), a gate electrode to extract electrons, and a set of electron focusing lenses (e.g., EinZel type electrostatic focusing lenses) to focus electrons to a small area or focal spot on a target (e.g. an anode). In some aspects, each anode can comprise a corresponding focal spot, generally designated 106. X-ray focal spots 106 can be distributed in space so that the x-ray beams 104 emitted from focal spots 106 can irradiate the ROI in an x-ray detector, generally designated 108, from different viewing angle(s) $\theta_1$, $\theta_2$. In some aspects, viewing angles $\theta_1$, $\theta_2$ can span an angular range substantially between 10 degrees and 90 degrees, depending on a given source-image distance. For example, viewing angles $\theta_1$, $\theta_2$ can each be approximately 16.91 degrees relative to a horizontal. In another example, viewing angles $\theta_1$, $\theta_2$ can be larger or smaller and/or can be two different angles. In some aspects, for example, x-ray source array 102 can be linear and can comprise a central x-ray focal spot with an area larger than the rest of the focal spots in the array. Such a configuration can allow a higher x-ray tube current.

X-ray detector 108 can be, for example, a high frame rate, digital area x-ray detector configured to continuously capture x-ray beams 104. In some aspects, it may be desirable for x-ray detector 108 to be configured with a fast frame rate. For example, x-ray detector 108 may comprise a frame rate in the order of approximately 1-100 frames per second. In some aspects, it may also be desirable that x-ray detector 108 comprises a high spatial resolution, with a pixel size in a range of approximately between, for example, 10×10 microns to 200×200 microns in order to detect projection images of patient P.

In some aspects, x-ray detector 108 can be positioned in an imaging plane that is substantially parallel to x-ray source array 102. For example, individual x-ray pixels, x-ray detector 108, and the ROI can be arranged such that the generated projection images are detected by the x-ray detector. In order for the x-ray beams 104 to image a targeted region of patient P, while still falling within the ROI in x-ray detector 108, it is desirable that the targeted region of patient P is positioned within the defined ROI. The x-ray beams 106 can then be directed to the ROI from several different angles. After passing through patient P, x-ray beams 104 can be detected by x-ray detector 108.

Figure 2A:
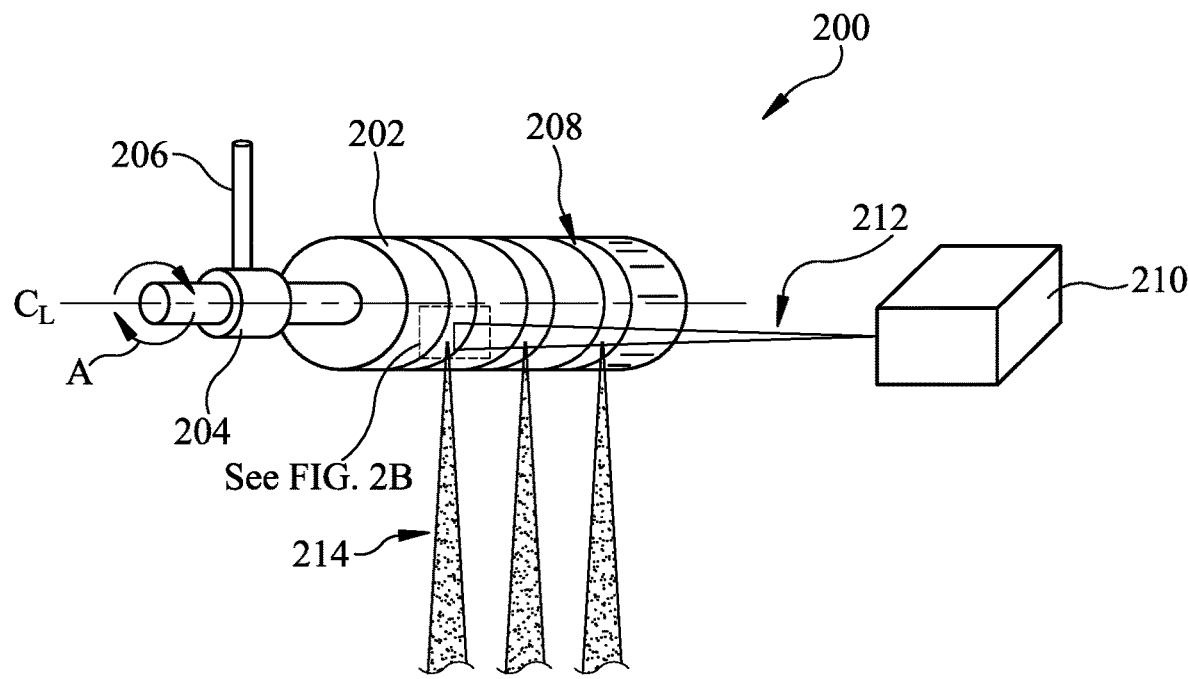
FIG. 2A is a schematic diagram illustrating an exemplary x-ray source array including a cylindrical rotation anode and a cathode for an s-DCT system according to some aspects of the present subject matter.
Figure 2B:
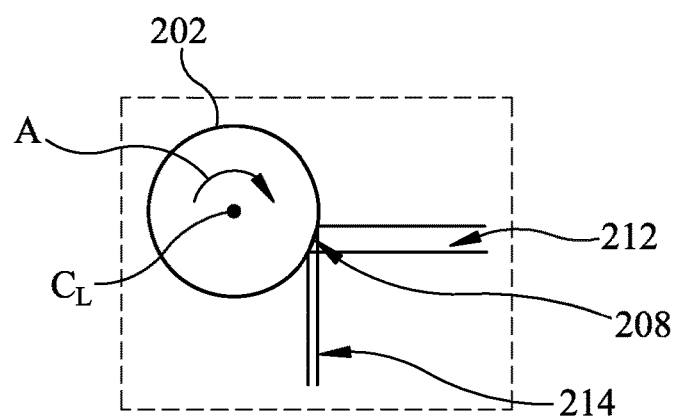
FIG. 2B is a detailed view illustrating a portion of the exemplary x-ray source array of FIG. 2A according to some aspects of the present subject matter.

Referring now to FIGS. 2A-2B, a schematic illustration of an exemplary x-ray source array, generally designated 200, is illustrated. X-ray source array 200 may be configured to be implemented as part of an s-DCT system, such as system 100 in FIG. 1. In some aspects, x-ray source array 200 can be configured as an x-ray source array capable of generating multiple x-ray beams.

As illustrated in FIG. 2A, x-ray source array 200 can comprise an anode, generally designated 202. Anode 202 can be a stationary structure comprised of one or more materials that provide the anode with a high melting temperature (e.g., tungsten), high heat capacitance (e.g., graphite), and/or a high thermal conductivity (e.g., copper). In some aspects, anode 202 may be configured as a rotating anode structure suitable to increase the thermal power. For example, anode 202 can be configured to rotate clockwise or counterclockwise about a centerline CL extending through a center of the anode structure. Arrow A provided in FIGS. 2A-2B illustrates a clockwise direction of rotation of anode 202 about centerline CL, although anode 202 is capable of rotating counterclockwise, as well. In some aspects, anode 202 may rotate via a shaft.

In some aspects, x-ray source array 200 can further comprise a high voltage (HV) anode contact, generally designated 204, and a HV feed, generally designated 206. For example, HV anode contact 204 and HV feed 206 are disposed at one end of the cylindrical anode structure, as illustrated in FIG. 2A. Alternatively, HV anode contact 204 and HV feed 206 may be disposed at the other end of the anode structure, or may each be disposed at opposing ends. In some aspects, one or more focal tracks, generally designated 208, may be disposed around an outer circumference of anode 202. Where there is more than one focal track 208 disposed on anode 202, focal tracks 208 may be spaced apart parallel to one another on the outer circumference of anode 202. For example, FIG. 2A illustrates three focal tracks 208 spaced substantially equidistant from one another on an outer circumference of anode 202.

Where x-ray source array 200 comprises a cathode, generally designated 210, electron beam(s), generally designated 212, may be generated by cathode 210 and directed to a focal spot within and along focal track(s) 208. For example, cathode 210 may comprise a CNT cathode positioned such that electron beam(s) 212 may hit a focal spot disposed within and along focal tracks 208 of anode 202 at an angle normal to an outer circumference of anode 202. Accordingly, and as illustrated in FIG. 2B, where anode 202 rotates about centerline CL, electron beam(s) 212 may bombard an anode surface at a focal point along focal tracks 208, which can then produce x-ray beam(s), generally designated 214, that are directed off of anode 202 at an angle approximately perpendicular relative to a direction of electron beam 212. In this manner, x-ray beams 214 may be directed from anode 202 towards a ROI in an x-ray detector. Notably, cathode 210 can be positioned such that the resultant x-ray beams are directable towards a ROI, regardless of the location of the detector.

Figure 3C:
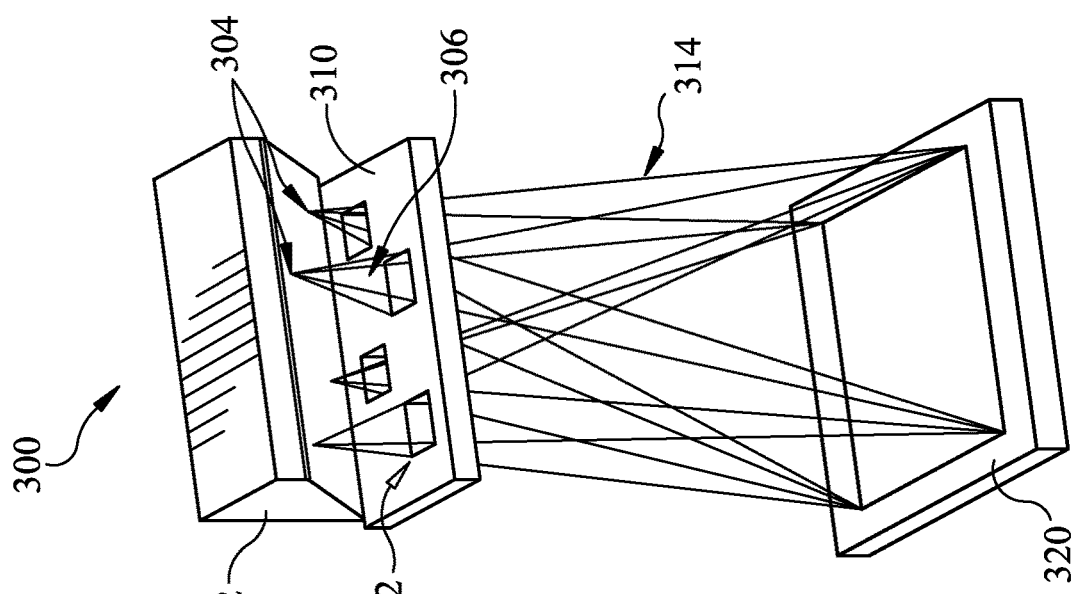
FIGS. 3A-3C are each schematic diagrams illustrating a front view, a side view, and a front perspective view, respectively, of a multiple beam collimator and a linear x-ray source array for an s-DCT system according to some aspects of the present subject matter.
Figure 3B:
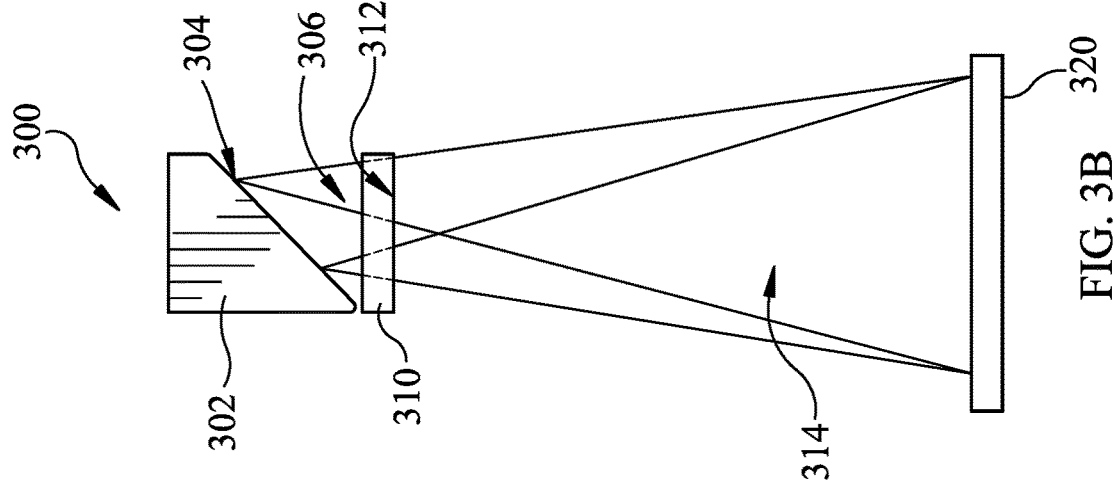
Figure 3A:
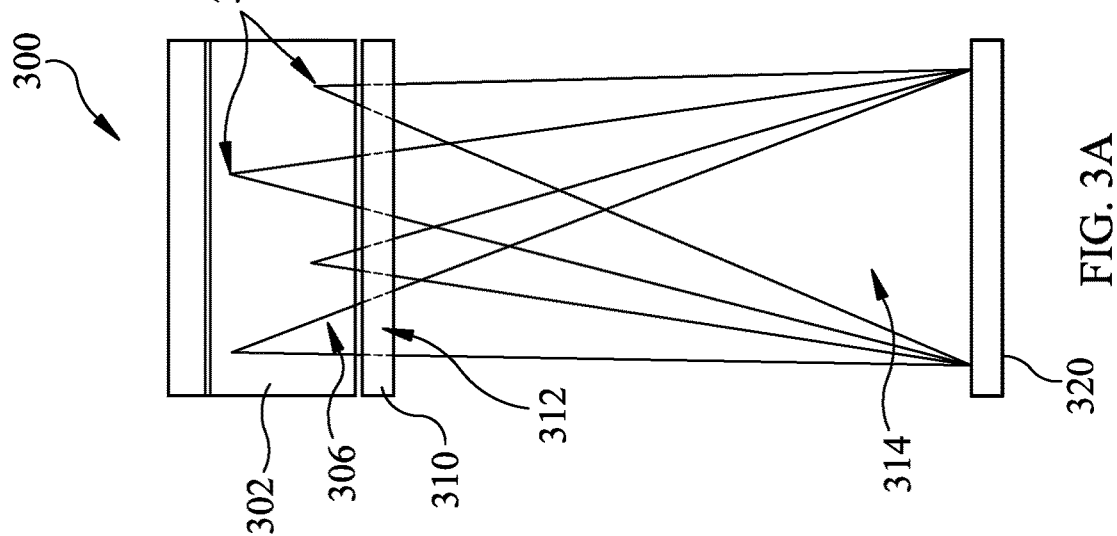

Referring now to FIGS. 3A-3C, schematic diagrams illustrating one embodiment of a collimator assembly, generally designated 300, in three differing views are provided. However, FIGS. 3A-3C and the accompanying description are merely for illustrative purposes and are in no way intended to limit the type of collimator that may be used with the systems and related methods described herein.

Collimator assembly 300 may be configured to be implemented in an s-DCT system (e.g., 100, FIG. 1) comprising an x-ray source array, generally designated 302, which may be an x-ray source array having similar components, configurations, and/or functionality to those described herein. X-ray source array 302 may comprise one or more focal spots, generally designated 304, through which x-ray beam (s), generally designated 306, may be generated. As illustrated in FIGS. 3A-3C, for example, x-ray source array 302 comprises four focal spots 304, each generating an x-ray beam 306. X-ray source array 302 may be, in some aspects, attached to or otherwise attachable to a collimator tray, generally designated 310, for collimating x-ray beam(s) 306 generated by one or more focal spots 304 to a same ROI in an x-ray detector, generally designated 320, that is disposed a predetermined distance from x-ray source array 302 and/or collimator tray 310.

Collimator tray 310 may, in some aspects, comprise a planar surface that is configured to be similarly sized, shaped, etc., to x-ray source 302. For example, collimator tray 310 may comprise a similar length and width to that of x-ray source array 302. In some aspects, collimator tray 310 may be fixed to x-ray source 302. For example, collimator tray 310 may be fixable along a lengthwise edge to a bottom edge of x-ray source 302. In this manner, collimator tray 310 may be collapsible or otherwise movable relative to x-ray source array 302 via hinges, joints, springs, and/or any other movable attachment devices. In some aspects, collimator tray 310 may comprise an array of openings, generally designated 312, which extend through a thickness direction of tray 310. For example, and as illustrated in FIGS. 3A-3C, there may be four openings 312 interspersed on a surface of collimator tray 310. Openings 312 may be provided in a pattern, such as, for example, a linear pattern, circular pattern, two dimensional pattern, etc. As shown in FIGS. 3A-3C, openings 312 are provided in a two dimensional pattern with two openings disposed towards a front edge of collimator tray 310 and two openings disposed towards a rear edge of collimator tray 310, where the rear edge is an edge of tray 310 where x-ray source array 302 is attachable or attached to the tray. Alternatively, openings 312 may be disposed in a non-patterned, random, and/or other position relative to one another. In some aspects, openings 312 may be sized and shaped for this purpose. As illustrated in FIGS. 3A-3C, openings 312 are provided as four similarly sized, square shaped openings, wherein each opening 312 collimates radiation generated from a corresponding focal spot 304 into a cone beam, generally designated 314, that substantially illuminates detector 320. As a result, openings 312 may be configured to confine x-ray beams 306 to a specific ROI. Moving, adjusting, and/or changing a position of openings 312 may be sufficient to confine x-ray beams 306 to a different ROI on x-ray detector 320.

Figure 4:
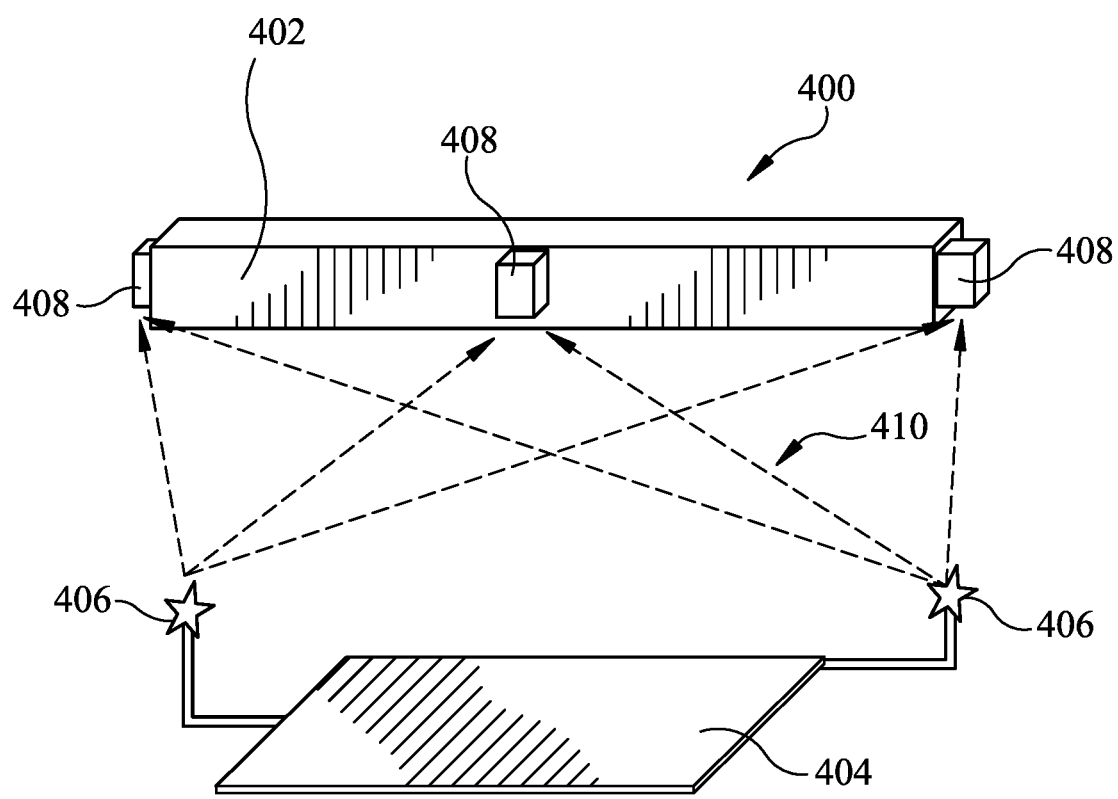
FIG. 4 is a schematic diagram illustrating an exemplary position sensing device for an s-DCT system according to some aspects of the present subject matter.

Referring now to FIG. 4, a schematic diagram of an exemplary s-DCT system, generally designated 400, is illustrated. Like s-DCT system 100 in FIG. 1, s-DCT system 400 can be used exclusively for imaging a patient's chest, while in other aspects s-DCT system 100 can be adapted for imaging a patient's breasts, mouth, abdomen, etc. In some aspects, s-DCT system 400 may comprise an x-ray source array, generally designated 402, and an x-ray detector, generally designated 404. X-ray source array 402 may comprise, in some aspects, a linear multi-beam x-ray source array, where multiple pixels are arranged in a one dimensional direction. As such, pixels of x-ray source array 402 may be disposed substantially parallel to an imaging surface of x-ray detector 404 so that x-ray detector may detect x-ray radiation generated by x-ray source array 402. Where x-ray source array 402 is not mechanically linked or otherwise coupled to x-ray detector 404 (e.g., via a mechanical arm (not shown)), a position sensing device or other similar type of apparatus may be utilized by s-DCT system 400 to determine precise positions of x-ray focal spots of x-ray source 402 with respect to x-ray detector 404. In some aspects, and in reference to FIG. 4, s-DCT system 400 comprises one or more emitter, generally designated 406, which are utilized in combination with one or more receptors, generally designated 408, to determine a relative position of x-ray detector 404 with respect to x-ray source array 402 using geometry calibration and/or other similar techniques.

In some aspects, one or more emitter 406 includes one or more signal emitter, fixture marker, etc., disposed relative to x-ray detector 404. For example, two signal emitters may be fixedly, or otherwise removably, disposed on opposing sides of x-ray detector 404. In this manner, one or more emitter 406 may be fixedly positioned at a known distance from x-ray focal spots disposed on x-ray source 402. In some aspects, one or more emitter 406 may be configured to emit a signal, ultrasound wave, etc., generally designated 410, which may be detected by one or more receiver 408 mounted on x-ray source 402. One or more receiver 408 may include one or more sensor, camera, etc., with each of the one or more receiver 408 being fixedly or otherwise removably disposed at predetermined locations on x-ray source 402. For example, there may be three cameras 408: a first camera being disposed in a center of x-ray source array 402 on a longitudinally extending surface normal to a surface in which pixels are disposed, a second camera being disposed at a surface of x-ray source array 402 that is normal to both the surface in which pixels are disposed and the surface on which the first camera is disposed, and a third camera being disposed at a surface of x-ray source array 402 opposing the surface at which the second camera is disposed. Other arrangements, numbers, etc., of one or more receivers 408 on x-ray source array 402 are also contemplated.

Alternatively, one or more receivers 408 may be mounted on a collimator (not shown) and/or any other structure that is not the x-ray source array, but that is configured to detect the signals and/or waves 410 emitted by one or more emitters 406. For example, one or more emitter can be mounted on x-ray source array 402 in proximity to one or more receiver, such a receiver being configured to detect a signal or light wave emitted by the one or more emitter and reflected by markers and/or structures (not shown) fixed on x-ray detector 404 and/or a collimator (not shown). Regardless, one or more receiver 408 may be configured to transmit the detected light, signal, etc., 410 to a computing platform for further processing and/or calibration, to be described in further detail below.

Figure 5:
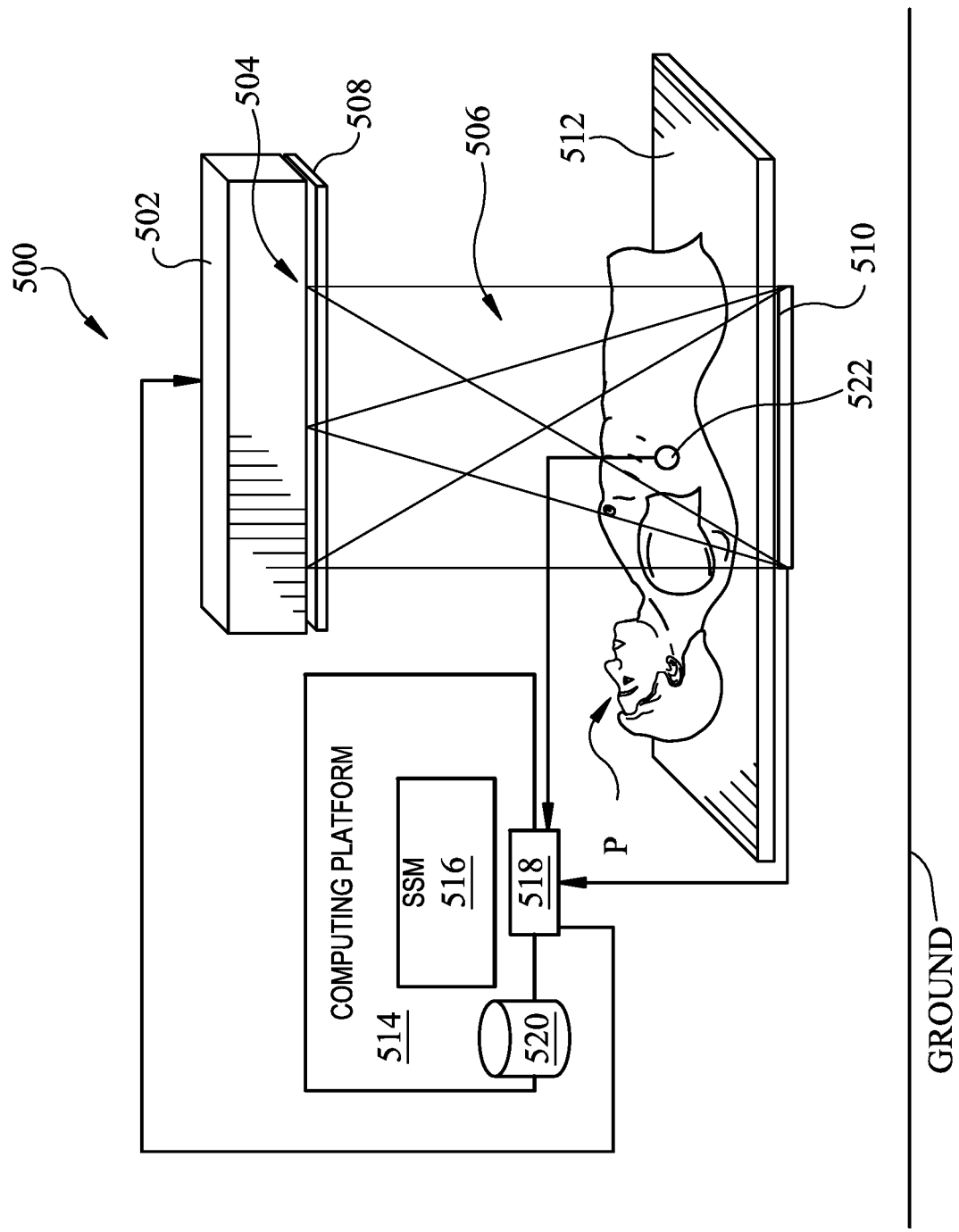
FIG. 5 is a schematic diagram illustrating an exemplary s-DCT system for a subject in a prone position according to some aspects of the present subject matter.

Referring now to FIG. 5, schematic diagram illustrating an exemplary s-DCT system, generally designated 500, for a patient P in a prone position is provided. Although s-DCT system 500 is illustrated for imaging a chest of a patient, it would be obvious to one of skill in the art that s-DCT system 500 may be utilized for imaging other portions of a patient P, e.g., breasts, mouth, abdomen, etc. In some aspects, s-DCT system 500 may be configured such that a patient P is lying in a prone position on a patient bed, as compared with s-DCT system 600 in FIG. 6, to be described in further detail, where a patient P is in an upright or standing position.

In some aspects, s-DCT system 500 comprises an x-ray source array, generally designated 502, which may be a multi-beam, linear x-ray source array, similar to ones described with regard to FIGS. 1 and 4. X-ray source array 502 may comprise a plurality of focal spots, generally designated 504. For example, a plurality of focal spots 504 may be linearly distributed along a bottom surface of x-ray source array 502, where the bottom surface is substantially parallel to a ground and/or an x-ray detector, generally designated 510. In some aspects, x-ray focal spots 504 may be positioned for directing the x-ray beams, generally designated 506, downwards, towards, and/or through an ROI, while first passing through a collimator, generally designated 508, which may enable x-ray beams 506 to be directed to the ROI from several different angles. As described previously, with regard to the embodiment of a collimator in FIGS. 3A-3C, collimator 508 may be attachable at at least one edge to x-ray source 502. In view of FIG. 5, in some aspects, collimator 508 may be substantially attached via a top surface to the bottom surface of x-ray source array 502. However, collimator 508 may be removable and/or tiltable at one edge relative to x-ray source array 502.

Accordingly, collimator 508 can confine x-ray beams 506 towards an ROI on x-ray detector 510. In some aspects, x-ray detector 510 is disposed underneath a patient bed 512 on which a patient P is in a prone position. X-ray source array 502, patient P, and x-ray detector 510 may all, thus, be aligned such that x-ray beams 506 are detected by x-ray detector 510 after passing through patient P. X-ray detector 510 may be configured to collect and/or transmit all or at least a portion of x-ray beams 506 that are detected. For example, x-ray detector 510 may be configured to collect and transmit detected x-ray beams 506 as x-ray signal data in an associated computing platform, generally designated 514. Computing platform 514 may comprise any platform configured for adjusting data collection, performing image acquisition, calibrating geometry, sensing position, reconstructing images, monitoring patients, and/or any other functions associated with s-DCT imaging. Computing platform 514 may be a stand-alone tool, device, or software executing on a processor. For example, computing platform 514 may comprise an electronic controller. In some aspects, computing platform 514 may comprise a single node or may be distributed across multiple computing platforms or nodes.

Computing platform 514 may include at least one s-DCT system module (SSM), generally designated 516, for adjusting data collection, performing image acquisition, calibrating geometry, sensing position, reconstructing images, monitoring patients, and/or any other functions associated with s-DCT imaging. Multiple modules may be utilized to perform multiple functionalities, however, for the sake of illustration only SSM 516 is illustrated in FIG. 5. In some aspects, a communications interface 518 may enable a user and/or node to interface with computing platform 514 and/or SSM 516 in order to perform associated functionality. Additionally, interface may allow transmission and/or receipt of information to and/or from computing platform 514 and/or SSM 516. In some aspects, computing platform 514 and/or SSM 516 may include or access data storage 520 containing data and/or images related to s-DCT imaging. For example, computing platform 514 and/or SSM 516 may access data storage 520 containing previous image acquisitions, mapped coordinate systems, image data, patient profiles, settings, or configurations. Exemplary data storage 520 may include non-transitory computer readable media, such as flash memory, random access memory, or other storage devices. In some embodiments, data storage 520 may be external to and/or or integrated with computing platform 514 and/or SSM 516.

Computing platform 514 and/or SSM 516 may comprise the functionality to control image acquisition of x-ray source array 502, while synchronizing data collection by x-ray detector 510, such that one or more projection image is recorded with radiation originating from each focal spot 504 in x-ray source array 502. In particular, computing platform 514 and/or SSM 516 may be configured to electronically control data collection of s-DCT system 500. For example, computing platform 514 and/or SSM 516 may be configured to switch on and off individual x-ray pixels in x-ray source array 502 for a predetermined dwell time, and may be configured to regulate an intensity of x-ray flux from each focal spot 504. Computing platform 514 and/or SSM 516 may also be configured to regulate an intensity of each focal spot 504 by either directly reading radiation from each focal spot 504, reading an x-ray tube current, and/or reading a cathode current. A size of each focal spot 504 and/or x-ray flux generated by each x-ray pixel may be individually adjusted by computing platform 514 and/or SSM 516. For example, computing platform 514 and/or SSM 516 may adjust a size of each focal spot 504 to approximately between 0.1 millimeters (mm) to 1.5 mm by adjusting electrical potentials of focusing electrodes in x-ray source array 502. Alternatively, focal spots 504 may be adjusted in size between approximately 0.05 mm and 2 mm.

In some aspects, computing platform 514 and/or SSM 516 may be configured to operate x-ray source array 502 up to approximately, for example, a 130 peak kilovoltage (kVp) and up to approximately between 10-20 milliampere (mA) tube current for each focal spot 504. However, a higher x-ray peak current of approximately between 50-100 mA may be obtained by increasing a carbon nanotube area and a size of each focal spot 504. To minimize current fluctuation and delay and to reduce pixel to pixel variation, computing platform 514 and/or SSM 516 may incorporate an electrical compensation loop to adjust gate voltage to maintain a constant preset emission current.

In some aspects, computing platform 514 and/or SSM 516 may be configured to acquire a scout view image of patient P once patient P is positioned. For example, computing platform 514 and/or SSM 516 may be configured to acquire a scout view image of patient P in a prone position on patient bed 512. In some aspects, acquiring a scout view may be desirable in order to ensure that an ROI is included in a field of view (FOV), check an exposure technique, acquire a baseline, etc. For example, from a scout view, kVp, mAs, number of projection images, angular span, etc., for subsequent projection views may be determined. In this manner, computing platform 514 and/or SSM 516 are capable of determining a number of projection views, angular coverage, x-ray energy, and image radiation dose prior to tomosynthesis scan.

In some aspects, computing platform 514 and/or SSM 516 may be configured to perform geometry calibration and/or position sensing of x-ray detector 510 relative to x-ray source array 502 when the two are not mechanically coupled or linked. For example, interface 518 of computing platform 514 and/or SSM 516 may receive data and/or signals that may be used by calibration software to determine a position of x-ray detector 510 relative to x-ray source array 502. For example, and referring back to FIG. 4, s-DCT system 400 may interface with computing platform 514, or similar. In such an example, SSM 516 (or similar) may comprise geometry calibration software that is capable of utilizing an x-ray image of calibration markers disposed on an x-ray source relative to an x-ray source to determine a position of an x-ray detector relative to an x-ray source.

In some aspects, computing platform 514 and/or SSM 516 may be configured to receive, via interface 518, all or at least a portion of x-ray signal data from detected from x-ray detector 510 for image reconstruction functionality. For example, computing platform 514 and/or SSM 516 may comprise an image reconstruction function (IRF) or other suitable functionality for reconstructing 3D tomosynthesis slice images of patient P. The images can be reconstructed by using a suitable technique such as filtered back projection (FBP), simultaneous iterative reconstruction technique (SIRT), or model based iterative reconstruction (MBIR), to obtain a 3D tomographic image of patient P. For example, computing platform 514 and/or SSM 516 can comprise a tomosynthesis reconstruction software package utilizing a variety of algorithms including shift-and-add, filtered back projection, ordered subsets convex maximum likelihood, etc. In some aspects, computing platform 514 and/or SSM 516 can be configured to acquire a plurality of projection images of patient P by simultaneously activating the plurality of x-ray pixels of x-ray source array 502 at a given time based on a multiplexing imaging scheme, and thereby synchronize x-ray exposure with data collection by x-ray detector 510, as described above. In some aspects, projection images can be de-multiplexed before tomosynthesis reconstruction software reconstructs tomography images of patient P using the plurality of projection images of patient P from different viewing angles.

In some aspects, computing platform 514 and/or SSM 516 may be configured to monitor physiological signals of patient P and to synchronize acquisition of the projection images with physiological gating signals so that projection images are only detected by x-ray detector 510 upon receiving a signal from a physiological monitor sensor (PMS), generally designated 522, attached to patient P. As illustrated in FIG. 5, PMS 522 is located on a chest of patient P. PMS 522 may be configured to monitor physiological signal(s) (e.g. respiratory and/or cardiac signals) of patient P and can communicate those signals to computing platform 514 and/or SSM 516 via interface 518. Once received, computing platform 514 and/or SSM 516 may be configured to define a physiological phase and a time window based off of the signals, such that computing platform 514 and/or SSM 516 can synchronize acquisition of the projection images with the physiological gating signals. For example, with respect to respiration of patient P, a time window can be configured as occurring at a same phase point over several respiratory cycles of a patient. Therefore, x-ray radiation will only occur during defined time windows of each respiration cycle. Since the images are obtained at this same phase point during a respiration cycle of each patient P, there is much less likelihood that dissimilar movement of patient P will occur to affect the image quality. Synchronization in this manner may enable projection images to only be acquired during a time window of the physiological phase, which advantageously significantly reduces or eliminates any blur caused by physiological motion of the patient between different projection images so that a full tomosynthesis scan can be completed either within a single respiratory cycle or over multiple respiratory cycles. Consequently, physiological gating can result in superior image quality without increasing the dose of radiation.

Figure 6:
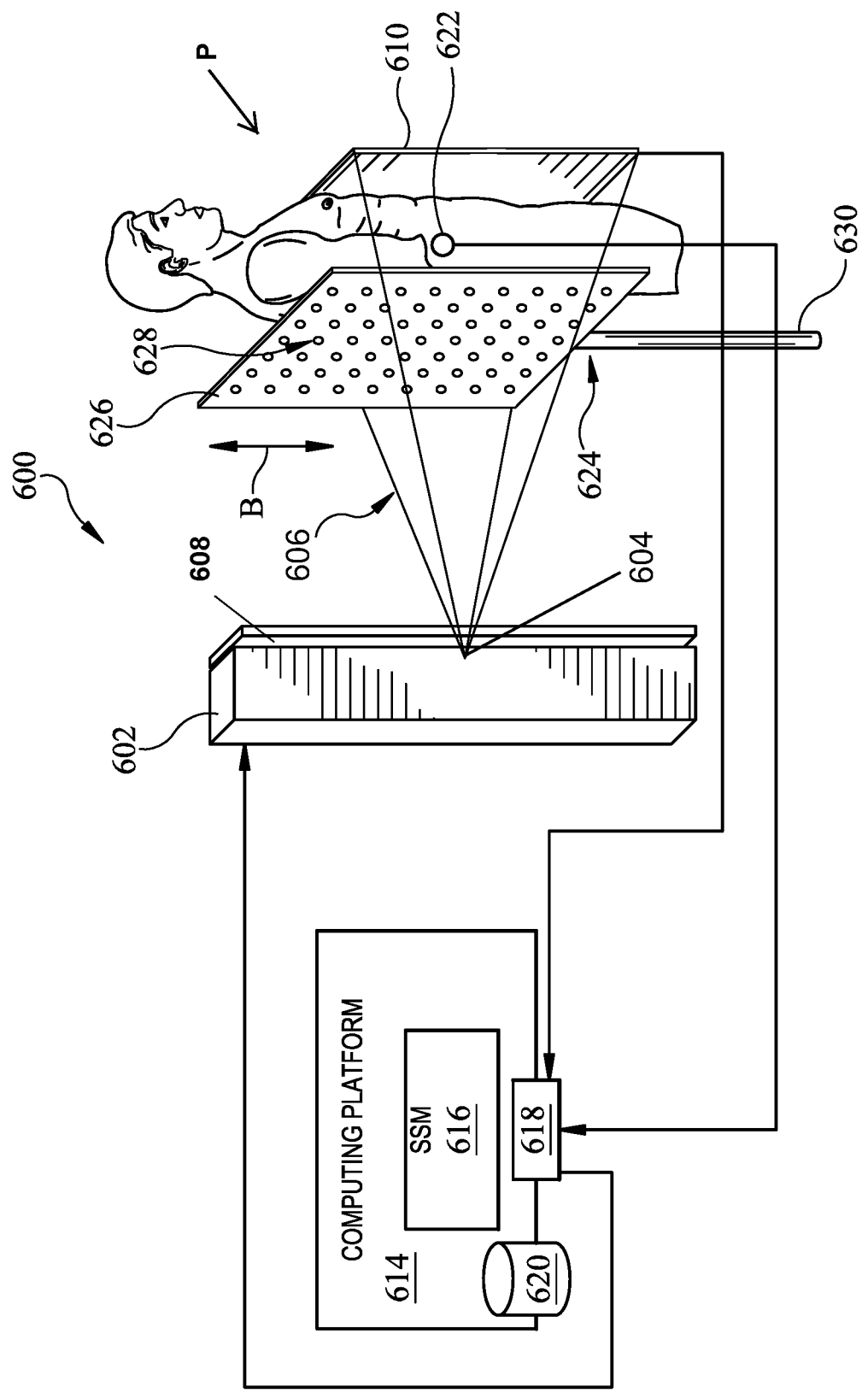
FIG. 6 is a schematic diagram illustrating an exemplary s-DCT system for a subject in an up-right position according to some aspects of the present subject matter.

Referring to FIG. 6, a schematic diagram illustrating an exemplary s-DCT system, generally designated 600, for a patient P in an up-right position is provided. Although s-DCT system 600 is illustrated for imaging a chest of a patient, it would be obvious to one of skill in the art that s-DCT system 600 may be utilized for imaging other portions of a patient, e.g., breasts, mouth, abdomen, etc. In some aspects, s-DCT system 600 may be configured such that a patient P is standing in an upright position relative to the ground.

Like s-DCT system 500, s-DCT system 600 may comprise similar features having substantially similar purposes. In particular, s-DCT system 600 comprises an x-ray source array, generally designated 602, which may be a multi-beam, linear x-ray source array, similar to ones described with regard to FIGS. 1, 4, and 5. X-ray source array 602 may comprise one or more focal spots, generally designated 604. For example, one focal spot 604 is provided along a longitudinally extending right facing surface of x-ray source array 602, where the right facing surface is substantially perpendicular to the ground and/or parallel to an x-ray detector, generally designated 610. In some aspects, x-ray focal spot 604 may be positioned for directing the x-ray beams, generally designated 606, rightwards, towards, and/or through an ROI, while first passing through a collimator, generally designated 608, which may enable x-ray beams 606 to be directed to the ROI from several different angles. As described previously, with regard to the embodiment of a collimator in FIGS. 3A-3C, collimator 608 may be attachable at at least one edge to x-ray source 602. In view of FIG. 6, in some aspects, collimator 608 may be substantially attached via a longitudinally extending left facing surface to the right facing surface of x-ray source array 602. However, collimator 608 may be removable and/or tiltable at one edge relative to x-ray source array 602.

Accordingly, collimator 608 can confine x-ray beams 606 towards an ROI on x-ray detector 610. In some aspects, x-ray detector 610 is disposed in a vertical plane substantially perpendicular to the ground and behind a patient P when a patient P is in a standing position. For example, and as illustrated in FIG. 6, x-ray detector 610 is disposed against a chest of patient P in a vertical plane that is substantially parallel to x-ray source array 602. X-ray source array 602, patient P, and x-ray detector 610 may all, thus, be aligned such that x-ray beams 606 are detected by x-ray detector 610 after passing through patient P.

X-ray detector 610 may be configured to collect and/or transmit all or at least a portion of x-ray beams 606 that are detected. For example, x-ray detector 610 may be configured to collect and transmit detected x-ray beams 606 as x-ray signal data in an associated computing platform, generally designated 614. Computing platform 614 may comprise any platform configured for adjusting data collection, performing image acquisition, geometry calibration, position sensing, image reconstruction, patient monitoring, primary beam sampling, and/or any other functions associated with s-DCT imaging. Computing platform 614 may be a stand-alone tool, device, or software executing on a processor. For example, computing platform 614 may comprise an electronic controller. In some aspects, computing platform 614 may comprise a single node or may be distributed across multiple computing platforms or nodes.

Computing platform 614 may include at least one SSM, generally designated 616, for adjusting data collection, performing image acquisition, calibrating geometry, sensing position, reconstructing images, monitoring patients, sampling primary beams, and/or any other functions associated with s-DCT imaging. Multiple modules may be utilized to perform multiple functionalities, however, for the sake of illustration only SSM 616 is illustrated in FIG. 6. In some aspects, a communications interface 618 may enable a user and/or node to interface with computing platform 614 and/or SSM 616 in order to perform associated functionality. Additionally, interface 618 may allow transmission and/or receipt of information to computing platform 614 and/or SSM 616. In some aspects, computing platform 614 and/or SSM 616 may include or access data storage 620 containing data and/or images related to s-DCT imaging. For example, computing platform 614 and/or SSM 616 may access data storage 620 containing previous image acquisitions, mapped coordinate systems, image data, patient profiles, settings, or configurations. Exemplary data storage 620 may include non-transitory computer readable media, such as flash memory, random access memory, or other storage devices. In some embodiments, data storage 620 may be external to and/or or integrated with computing platform 614 and/or SSM 616.

In some aspects, computing platform 614 and/or SSM 616 may comprise the functionality to control image acquisition of x-ray source array 602, while synchronizing data collection by x-ray detector 610, such that one or more projection image is recorded with radiation originating from each focal spot 604 in x-ray source array 602. In some aspects, computing platform 614 and/or SSM 616 may be configured to acquire a scout view image of patient P once patient P is positioned. For example, computing platform 614 and/or SSM 616 are configured to acquire a scout view image of patient P in a standing position. In this manner, computing platform 614 and/or SSM 616 are capable of determining a number of projection views, angular coverage, x-ray energy, and image radiation dose prior to tomosynthesis scan. In some aspects, computing platform 614 and/or SSM 616 may be configured to perform geometry calibration and/or position sensing of x-ray detector 610 relative to x-ray source array 602 when the two are not mechanically coupled or linked. In some aspects, computing platform 614 and/or SSM 616 may be configured to receive, via interface 618, all or at least a portion of x-ray signal data from detected from x-ray detector 610 for image reconstruction functionality. In some aspects, computing platform 614 and/or SSM 616 may be configured to monitor physiological signals of patient P and to synchronize acquisition of the projection images with physiological gating signals so that projection images are only detected by x-ray detector 610 upon receiving a signal from a PMS, generally designated 622, attached to patient P. As illustrated in FIG. 6, PMS 622 is located on a side of patient P. PMS 622 may be configured to monitor physiological signal(s) (e.g. respiratory and/or cardiac signals) of patient P and can communicate those signals to computing platform 614 and/or SSM 616 via interface 618.

Accordingly, computing platform 614 and/or SSM 616 may be configured with the same functionality as computing platform 514 and/or SSM 516 illustrated in FIG. 5, but in an s-DCT system where patient P is in a standing position. In addition, though, computing platform 614 and/or SSM 616 may be further configured to reduce photon scatter by performing beam sampling.

In particular, in conventional x-ray imaging it is known that detected x-ray photons are composed of primary beam photons (i.e., those photons that travel from an x-ray source to an x-ray detector without altering their directions) and scatter photons (i.e., those photons that undergo one or several scattering(s) by an object, hence change their direction). However, only primary photons detected are useful for imaging since the scatter photons may add to noise and degrade image contrast and contrast-to-noise ratio. In chest imaging applications, specifically, it is known that a scatter-to-primary photon ratio can vary from approximately 0.5 to 5 depending on a ROI and a size of a patient. Thus, it may be advantageous to remove and/or correct scatter photons. In order to do so, a primary beam sampling apparatus (PSA), generally designated 624, may be implemented to estimate and subtract scatter photons.

In some aspects, and in reference to FIG. 6, PSA 624 can be implemented in s-DCT system 600 and can be positioned between the x-ray 610 source array 602 and patient P. In some aspects, PSA 624 can comprise an anti-scattering plate or grid, generally designated 626, configured with a substantially opaque and/or planar surface and disposed in a vertical plane in alignment with and substantially parallel to x-ray source array 602 and x-ray detector 610. For example, grid 626 can be disposed so that a right facing surface is substantially adjacent to a back of patient P, such that patient P is sandwiched between x-ray detector 610 and grid 626. In some aspects, grid 626 is sized relative to x-ray detector 610. For example, in FIG. 6, grid 626 comprises a width that is less than a width of x-ray detector 610. Alternatively, grid 626 may be larger than or substantially similar in size with x-ray detector 610. In some aspects, grid 626 consists of a material that enables transmission of x-ray beams 606. In other aspects, grid 626 is configured with a two-dimensional matrix of openings, generally designated 628, running both parallel and perpendicular to x-ray source array 602, which are configured to allow transmission of x-ray beams 606 therethrough. Openings 628 may comprise various shapes and/or sizes or may be homogenous. For example, openings 628 may comprise circular openings with an opening area being approximately three percent (3%) or less of a target ROI. In this manner, any additional dose associated with the PSA image is minimal.

Accordingly, x-ray photons detected at x-ray detector 610 at positions in line with openings 628 may correspond to accurate measurements of a primary photon beam passing through patient P. For example, two sets of projection images using the same parameters may be acquired and provided to computing platform 614 and/or SSM 616 via interface 618 for processing of each. In this example, one set of projection images may be composed of one or more scan including PSA 624 and one set may be composed of one or more scan not including PSA 624. From the samplings of the primary beam, the scatter photon count at these positions can be obtained, from which an overall scatter map of patient P (without the presence of PSA 624) can be accurately estimated by computing platform 614 and/or SSM 616. Then the estimated scatter photon map can be subtracted from the image of patient P without PSA 624 in order to provide a scatter corrected projection image of patient P without PSA 624. Notably, spare sampling of a scatter map may be sufficient to estimate an overall scatter map as a scatter image of patient P is generally smooth depending on a distance scale between openings 628. Scatter corrected projection images with reduced noise from the scatter photons may then be used for tomosynthesis reconstruction at computing platform 614 and/or SSM 616 to obtain a 3D image(s) with substantially improved image contrast and contrast to noise ratio.

In some aspects, a position of PSA 624 relative to x-ray source array 602 and/or x-ray detector 610 may be controllable by computing platform 614 and/or SSM 616 via interface 618. Accordingly, grid 626 is configured to be movable relative to at least one direction by a sliding apparatus or mechanism, generally designated 630. For example, grid 626 is configured to be movable along a vertical direction, illustrated by arrow B, through movement of grid 626 along sliding mechanism 630. Grid 626 may also or alternately be moved in a horizontal direction relative to the ground. In some aspects, a user may interface with computing platform 614 and/or SSM 616 via interface 618 in order to control a position of PSA 624 relative to an ROI. For example, different ROIs being targeted may require vertical movement of grid 626. PSA 624 is also configured to be inserted and/or removed rapidly between patient P and x-ray source array 602 via sliding apparatus 630. In some aspects, sliding apparatus 630 may comprise a mechanical mechanism that allows grid 626 to slide along a length of the apparatus. For example, a track, groove, or other suitable configuration may allow a corresponding component on grid 626 to controllably move along a length of sliding apparatus 630. Other techniques for moving grid 626 relative to x-ray source array 602 are also contemplated. In addition, PSA 624 or any type of scatter reduction methodology may be implemented in an s-DCT system where patient P is in a position other than a standing position (e.g., s-DCT 500, FIG. 5).

Figure 7:
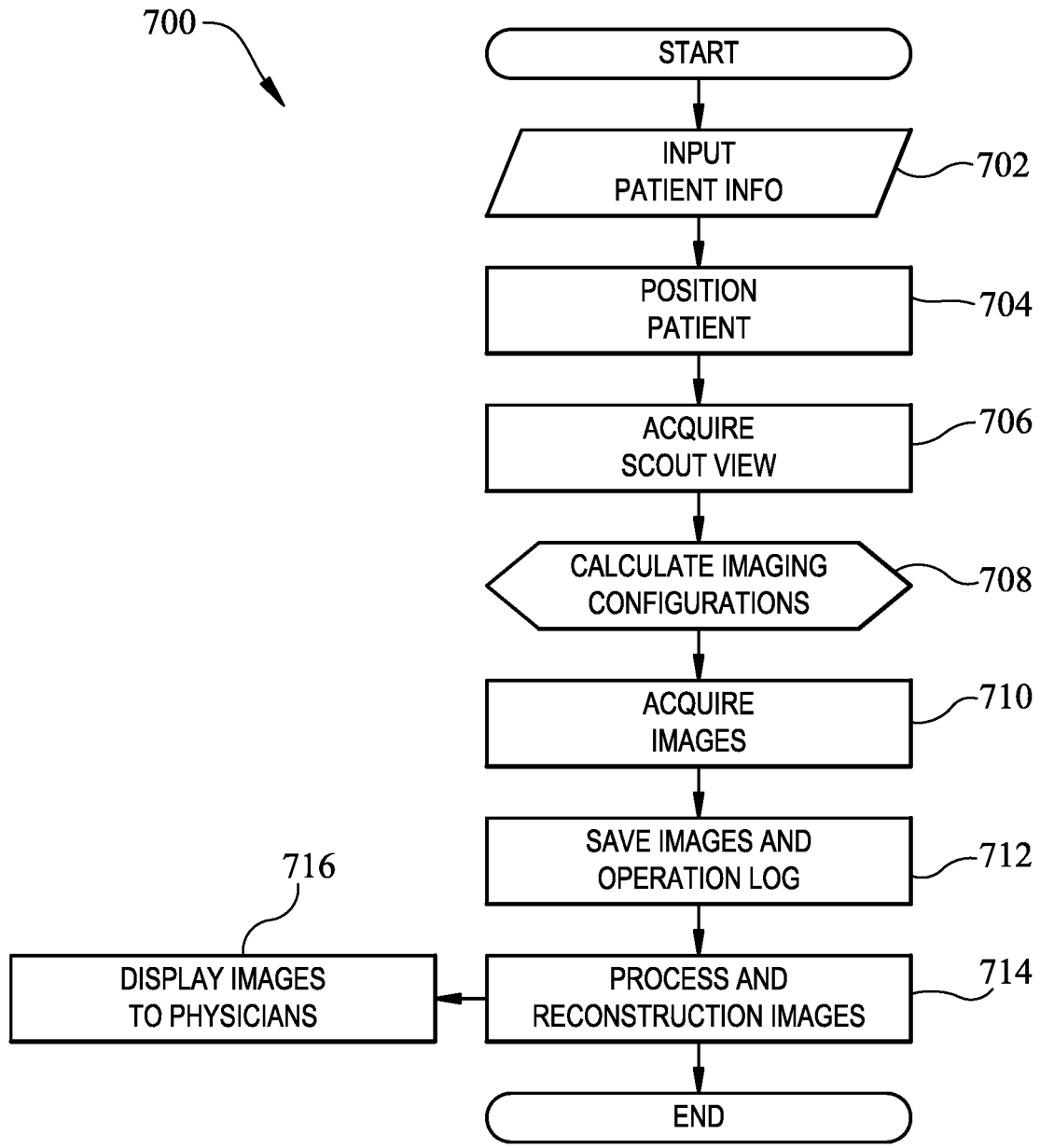
FIG. 7 is a flow diagram illustrating an exemplary process of acquiring a fast tomography image using an s-DCT system according to some aspects of the present subject matter.

Referring to FIG. 7, a flow diagram illustrating an exemplary process, generally designated 700, of acquiring a fast tomography image using an s-DCT system, as described herein, is provided. An s-DCT system may include any of the systems described herein, including, but not limited to s-DCT systems where a patient is in a prone position, a standing position, etc. However, process 700 may also be implemented using a stationary digital tomosynthesis system for tomography imaging applications other than of the chest variety.

In step 702, patient information may be input, via interface, into an exemplary computing platform. For example, patient information may be automatically transmitted to a computing platform and/or it may be manually entered by a user.

In step 704, a patient can be positioned relative to an x-ray source array and/or an x-ray detector. For example, a patient may be positioned in a prone position (e.g., s-DCT system 500, FIG. 5) or an upright position (e.g., s-DCT system 600, FIG. 6). Alternatively, a patient may also be positioned in a different position (e.g., a seated position).

In step 706, a scout view of a preliminary image can be acquired. For example, computing platform may control acquisition of a scout view of a preliminary image in order to calculate image configurations (e.g., in step 708).

In step 708, image configurations may be calculated based on a scout view of a preliminary image acquired in step 706. For example, a scout view of a preliminary image may be utilized for determining kVps, mAs, number of projection images, the angular span, etc.

In step 710, projection images may be acquired. For example, a computing platform (e.g., a controller) may activate individual pixels in an x-ray source array in order to irradiate a patient with x-ray beams. The computing platform and/or controller can likewise control an x-ray detector to detect projection images of a patient in order to generate and, thus acquire projection images of the patient.

In step 712, projection images and an operation log acquired in step 710 can be collected and saved to data storage associated with the computing platform.

In step 714, a module associated with a computing platform may process the projection images in order to reconstruct tomography images. For example, IRF software implemented by a module and/or computing platform may be configured to access stored projection images and/or operation log(s) in order to reconstruct tomography images of the patient based on the projection images of the patient. In some aspects, any suitable technique can be utilized by the IRF software for reconstructing the tomography images.

In step 716, tomography images may optionally be displayed at a display associated with a computing platform. For example, a physician or other interested party may access reconstructed tomography images for a specific patient from a specific imaging session for analysis and/or diagnosis.

Figure 8:
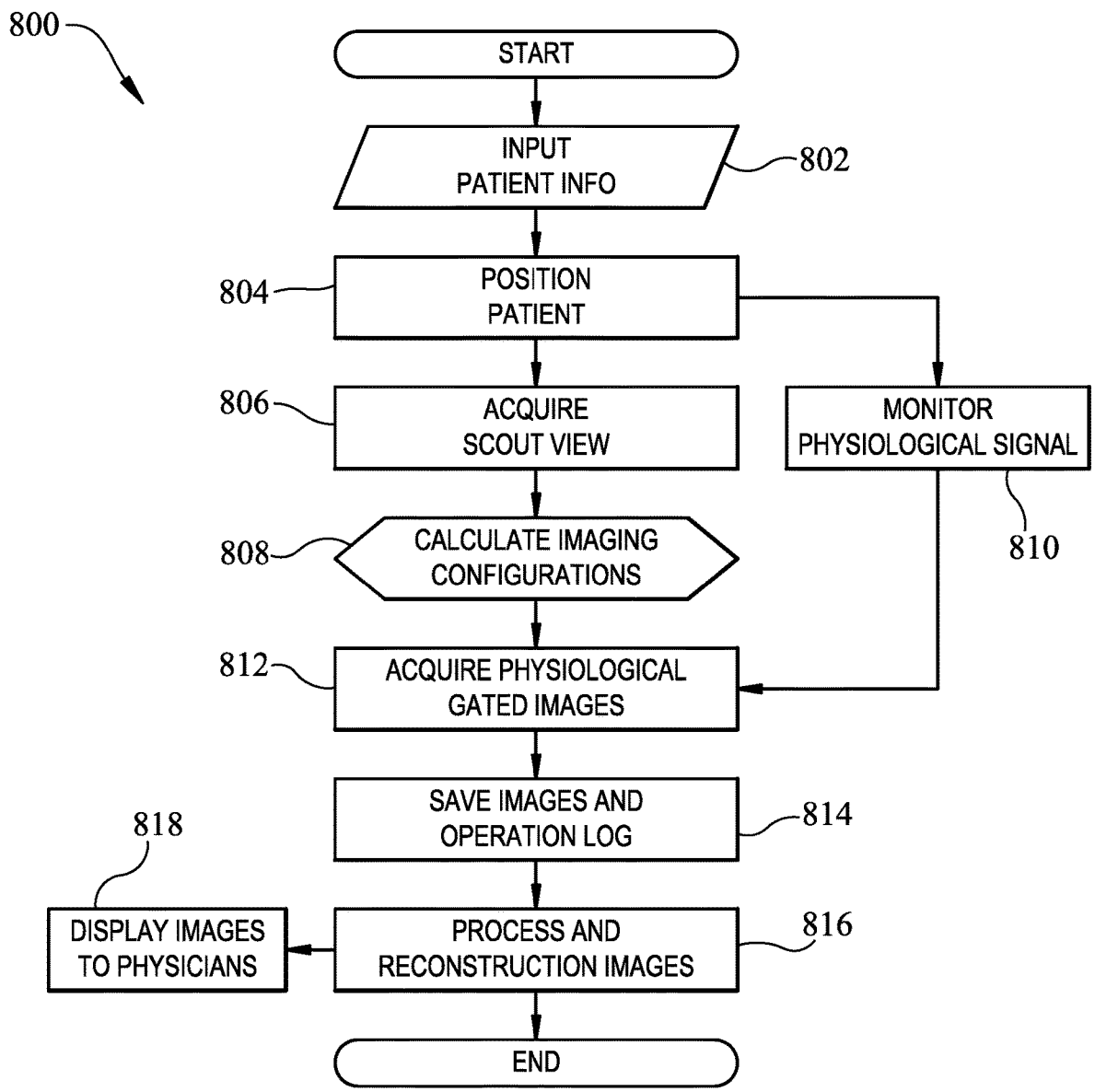
FIG. 8 is a flow diagram illustrating an exemplary process of acquiring a respiration gated tomography image using an s-DCT system according to some aspects of the present subject matter.

Referring to FIG. 8, a flow diagram illustrating an exemplary process, generally designated 800, of acquiring a fast tomography image using a gated s-DCT system as described herein is provided. A gated s-DCT system may include any of the systems described herein, including, but not limited to gated s-DCT systems where a patient is in a prone position, a standing position, etc. However, process 800 may also be implemented using a gated stationary digital tomosynthesis system for tomography imaging applications other than of the chest variety.

In step 802, patient information may be input, via interface, into an exemplary computing platform. For example, patient information may be automatically transmitted to a computing platform and/or it may be manually entered by a user.

In step 804, a patient can be positioned relative to an x-ray source array and/or an x-ray detector. For example, a patient may be positioned in a prone position (e.g., s-DCT system 500, FIG. 5) or an upright position (e.g., s-DCT system 600, FIG. 6). Alternatively, a patient may also be positioned in a different position (e.g., a seated position).

In step 806, a scout view of a preliminary image can be acquired. For example, computing platform may control acquisition of a scout view of a preliminary image in order to calculate image configurations (e.g., in step 808).

In step 808, image configurations may be calculated based on a scout view of a preliminary image acquired in step 806. For example, a scout view of a preliminary image may be utilized for determining kVps, mAs, number of projection images, the angular span, etc.

In step 810, physiological signals may be monitored. In some aspects, after patient is positioned in step 804, a PMS may be attached to the patient in order to monitor physiological signal(s) of the patient (e.g. respiratory and/or cardiac signals). The PMS can communicate the signals to a computing platform that may be configured to synchronize the physiological signal(s) with acquisition of the projection images. In this manner, projection images of a patient may only be acquired during a defined time window of a physiological phase.

In step 812, where a PMS is being used, physiological gated images may be acquired by a computing platform. In some aspects, a computing platform (e.g., a controller) may activate individual pixels in an x-ray source array in order to irradiate a patient with x-ray beams during a defined time window determined in step 810. The time window can be defined such that images are acquired only at certain phase points during a physiological cycle of the patient, based on information provided by the physiological gating signals. The computing platform and/or controller can likewise control an x-ray detector to detect projection images of a patient in order to generate and, thus acquire physiological gated projection images of the patient.

In step 814, physiological gated projection images and an operation log acquired in step 812 can be collected and saved to data storage associated with the computing platform.

In step 816, a module associated with a computing platform may process the physiological gated projection images in order to reconstruct tomography images. For example, IRF software implemented by a module and/or computing platform may be configured to access stored physiological gated projection images and/or operation log (s) in order to reconstruct tomography images of the patient based on the physiological gated projection images of the patient. In some aspects, any suitable technique can be utilized by the IRF software for reconstructing the tomography images.

In step 818, tomography images may optionally be displayed at a display associated with a computing platform.

For example, a physician or other interested party may access reconstructed tomography images for a specific patient from a specific imaging session for analysis and/or diagnosis.

Figure 9:
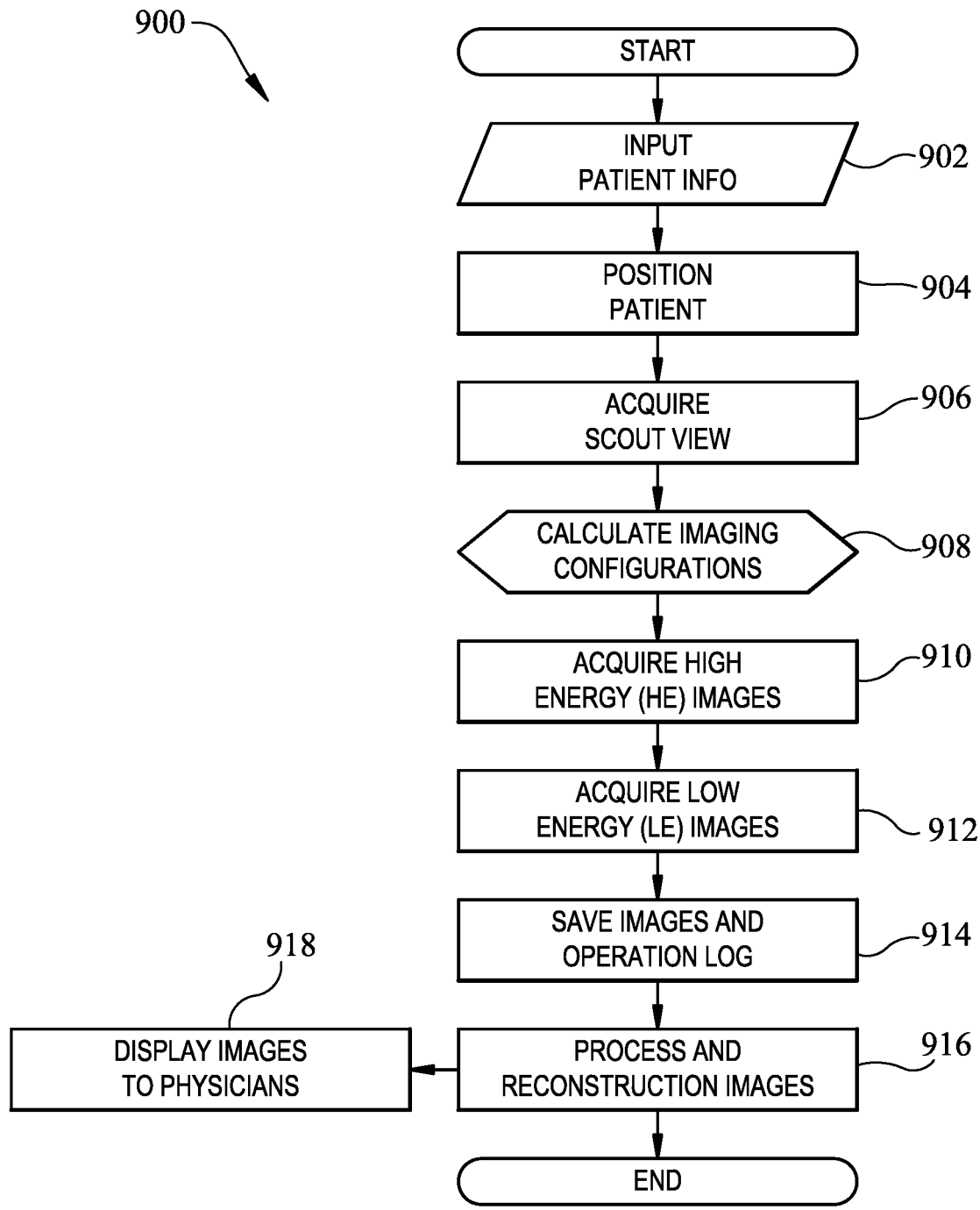
FIG. 9 is a flow diagram illustrating an exemplary process of acquiring a dual energy gated tomography image using an s-DCT system according to some aspects of the present subject matter.

Referring to FIG. 9, a flow diagram illustrating an exemplary process, generally designated 900, of acquiring a dual energy or multiple energy tomography image using a dual energy s-DCT system, as described herein, is provided. For example, in a dual energy tomography imaging process, for each object being imaged, two complete sets of x-ray projection images can be collected. A first set can be collected at an x-ray energy 1, while a second set can be collected at an x-ray energy 2, where x-ray energy 1 is different from x-ray energy 2. In one aspect, the two sets of x-ray images may be collected at two different x-ray anode voltages. The two sets of images can then be processed, reconstructed, and subtracted to enhance contrast for certain features. In another aspect, at each viewing angle, two projection images may be taken, one at x-ray energy 1, the other at x-ray energy 2. As described in reference to process 900, a dual energy s-DCT system may include any of the systems described herein, including, but not limited to dual energy s-DCT systems where a patient is in a prone position, a standing position, etc. However, process 900 may also be implemented using a stationary digital tomosynthesis dual energy system for tomography imaging applications other than of the chest variety.

In step 902, patient information may be input, via interface, into an exemplary computing platform. For example, patient information may be automatically transmitted to a computing platform and/or it may be manually entered by a user.

In step 904, a patient can be positioned relative to an x-ray source array and/or an x-ray detector. For example, a patient may be positioned in a prone position (e.g., s-DCT system 500, FIG. 5) or an upright position (e.g., s-DCT system 600, FIG. 6). Alternatively, a patient may also be positioned in a different position (e.g., a seated position).

In step 906, a scout view of a preliminary image can be acquired. For example, computing platform may control acquisition of a scout view of a preliminary image in order to calculate image configurations (e.g., in step 908).

In step 908, image configurations may be calculated based on a scout view of a preliminary image acquired in step 906. For example, a scout view of a preliminary image may be utilized for determining kVps, mAs, number of projection images, the angular span, etc.

In step 910, a first set of high energy (HE) images at a first voltage may be acquired by a computing platform. In some aspects, a computing platform (e.g., a controller) may activate individual pixels in an x-ray source array in order to irradiate a patient with x-ray beams. The computing platform and/or controller can likewise control an x-ray detector to detect projection images of a patient in order to generate and, thus acquire HE projection images of the patient.

In step 912, a second set of low energy (LE) images at a second voltage, where the second voltage is lower than the first voltage, may be acquired by a computing platform. In some aspects, a computing platform (e.g., a controller) may activate individual pixels in an x-ray source array in order to irradiate a patient with x-ray beams. The computing platform and/or controller can likewise control an x-ray detector to detect projection images of a patient in order to generate and, thus acquire LE projection images of the patient.

In step 914, the HE and LE projection images and an operation log associated with each set of images, as acquired in steps 910-912 can be collected and saved to data storage associated with the computing platform.

In step 916, a module associated with a computing platform may process the HE and LE projection images in order to reconstruct tomography images. For example, IRF software implemented by a module and/or computing platform may be configured to access stored HE and LE projection images and/or operation log(s) in order to reconstruct tomography images of the patient based on the HE and LE projection images of the patient. In some aspects, any suitable technique can be utilized by the IRF software for reconstructing the tomography images.

In step 918, tomography images may optionally be displayed at a display associated with a computing platform. For example, a physician or other interested party may access reconstructed tomography images for a specific patient from a specific imaging session for analysis and/or diagnosis.

Figure 10:
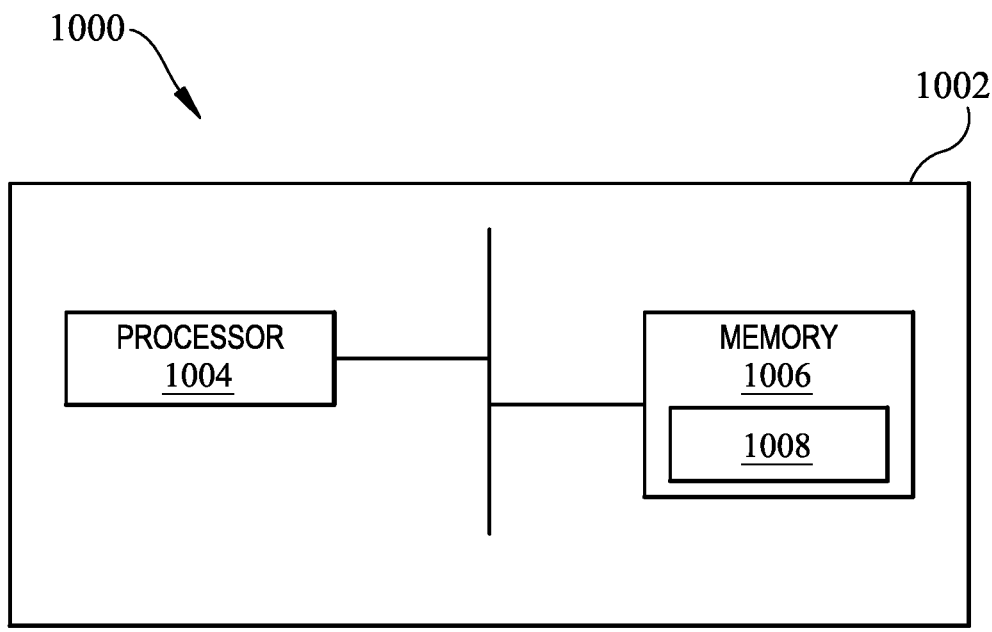
FIG. 10 is a high level block diagram illustrating an exemplary general purpose computer system suitable for use in acquiring tomography images using an s-DCT system according to some aspects of the present subject matter.

Referring to FIG. 10, a high level block diagram, generally designated 1000, of exemplary components of a computing platform, generally designated 1002, for use in performing the functions described herein, is provided As depicted in FIG. 10, computing platform 1002 comprises a processor, generally designated 1004, a memory, generally designated 1006 communicatively connected via a system bus. In some aspects, processor 1004 can comprise a microprocessor, central processing unit (CPU), or any other like hardware based processing unit. In some aspects, an SSM, generally designated 1008, with functionality as discussed herein, can be stored in memory 1006, which can comprise random access memory (RAM), read only memory (ROM), optical read/write memory, cache memory, magnetic read/write memory, flash memory, or any other non-transitory computer readable medium. In some embodiments, processor 1004 and memory 1006 can be used to execute and manage the operation of SSM 1008. Thus, when configured with SSM 1008, computing platform 1002 becomes a special purpose computing platform that improves the technological area of acquiring s-DCT images by eliminating mechanical motion of traditional s-DCT systems. Specifically, coordination between computing platform 1002 and an s-DCT system (e.g., 500, FIG. 5) is necessarily rooted in computer technology in order to overcome a problem specifically arising in the realm of computer networks (i.e., acquiring s-DCT images with higher quality and resolution and in a shorter scanning time).

Figure 11:
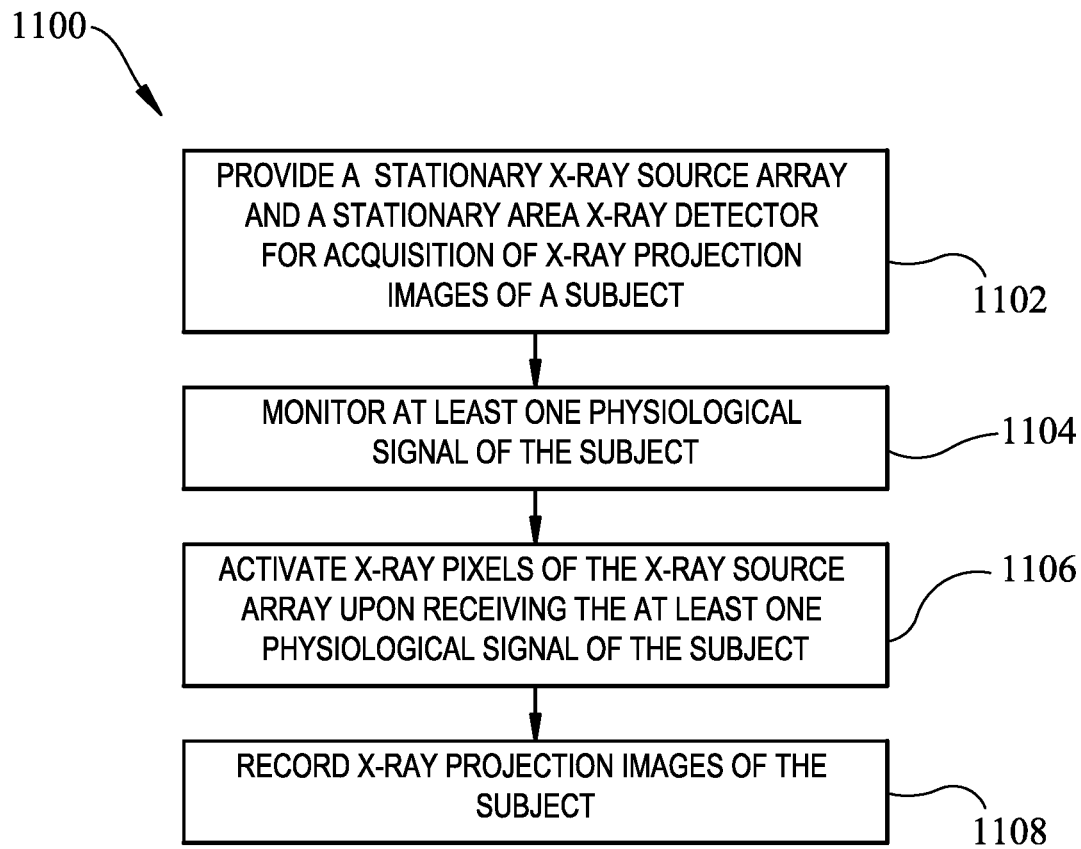
FIG. 11 is a flow diagram illustrating an exemplary method for stationary digital tomography imaging according to some aspects of the present subject matter.

Referring to FIG. 11, flow diagram, generally designated 1100, illustrating an exemplary method for stationary digital tomography imaging, as described herein, is provided.

In step 1102, a stationary x-ray source array comprising an array of spatially distributed x-ray pixels configured to generate x-ray beams at different viewing angles relative to a subject to be imaged that is stationary and a stationary area x-ray detector positioned substantially parallel to a plane of the x-ray source array and configured to record x-ray projection images of the subject from the different viewing angles for tomosynthesis reconstruction are each provided.

In step 1104, a physiological gating apparatus monitors at least one physiological signal of the subject, the physiological gating apparatus defining a physiological phase and a time window based on the at least one physiological signal during which the x-ray projection images of the subject from the different viewing angles are acquirable.

In step 1106, the computing platform activates the x-ray pixels upon receiving the at least one physiological signal in order to synchronize x-ray exposure with the at least one physiological signal of the subject.

In step 1108, x-ray projection images of the subject from the different viewing angles are recorded.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:

1. A method of producing fast tomography images of an object, the method comprising:
   providing an X-ray source array configured to generate cone-beam X-ray radiation from an array of spatially distributed X-ray focal spots;
   collimating the X-ray radiation from each of the X-ray focal spots of the X-ray source array to a region of interest in an area X-ray detector;
   detecting and collecting, at the area X-ray detector, one or more first projection images of the object, wherein a primary beam sampling apparatus is between the X-ray source array and the area X-ray detector when the one or more first projection images are collected;
   detecting and collecting, at the area X-ray detector, one or more second projection images of the object, wherein the primary beam sampling apparatus is not between the X-ray source array and the area X-ray detector when the one or more second projection images are collected;
   estimating a scatter signal profile of the object from the one or more first projection images;
   subtracting the scatter signal profile of the object from the one or more second projection images to produce one or more projection images with a reduced scatter signal; and
   reconstructing tomography images based on the projection images with a reduced scatter signal;
   wherein the primary beam sampling apparatus comprises an anti-scattering grid comprising a two-dimensional matrix of openings that together define an opening area of 3% or less of a region of interest (ROI) of the area X-ray detector to minimize an additional dose of X-ray radiation to the object when the one or more first projection images of the object are collected; and
   wherein the openings allow transmission of X-ray photons therethrough.

2. The method of claim 1, further comprising disposing the area X-ray detector in a vertical plane substantially perpendicular to a ground and positioning the object between the X-ray source array and the area X-ray detector.

3. The method of claim 1, further comprising acquiring a scout view image of the object and determining a number of projection views, angular coverage, X-ray energy, and image radiation dose prior to detecting and collecting the projection images of the object.

4. The method of claim 1, wherein detecting and collecting the projection images of the object comprises:
   monitoring physiological gating signals of the object using a physiological monitoring sensor (PMS) attached to the object; and
   synchronizing acquisition of the projection images with physiological gating signals.

5. The method of claim 4, further comprising detecting projection images at the X-ray detector upon receiving a signal from the PMS.

6. The method of claim 4, wherein the physiological gating signals comprise respiratory or cardiac signals.

7. The method of claim 1, wherein estimating and subtracting the scatter signal profile of the object comprises:
positioning the primary beam sampling apparatus between the X-ray source array and the object;
capturing the one or more first projection images of the object, wherein the first one or more projection images have reduced or eliminated X-ray photon scatter in one or more sampling region;
removing the primary beam sampling apparatus from between the X-ray source array and the object;
capturing the one or more second projection images of the object, wherein X-ray photon scattering of the second one or more projection images is not reduced;
obtaining a sampling of the scatter signal profile of the object by comparing the one or more first projection images of the object to the one or more second projection images of the object; and
subtracting the scatter signal profile from the one or more second projection images to obtain the projection images with a reduced scatter signal.

8. The method of claim 7, wherein:
the anti-scattering grid is disposed in a vertical plane in alignment with and substantially parallel to the X-ray source array and the area X-ray detector; and
the openings of the two-dimensional matrix of openings of the anti-scattering grid run both parallel and perpendicular to the X-ray source array.

9. The method of claim 1, wherein the primary beam sampling apparatus is configured to move horizontally or vertically with respect to a ground.

10. A system for producing fast tomography images of an object, the system comprising:
an X-ray source array configured to generate cone-beam X-ray radiation from an array of spatially distributed X-ray focal spots of the X-ray source array;
an area X-ray detector configured to detect X-ray radiation transmitted from the X-ray source array;
a collimator positioned between the X-ray source array and a region of interest on the area X-ray detector, the collimator being configured to collimate X-ray radiation from each of the X-ray focal spots of the X-ray source array to the region of interest of the area X-ray detector;
a primary beam sampling apparatus, wherein:
the area X-ray detector is configured to detect and collect one or more first projection images of the object when the primary beam sampling apparatus is between the X-ray source array and the area X-ray detector; and
the area X-ray detector is configured to detect and collect one or more second projection images of the object when the primary beam sampling apparatus is not between the X-ray source array and the area X-ray detector; and
a computing platform comprising one or more processors, the computing platform being configured to:
estimate a scatter signal profile of the object from the one or more first projection images;
subtract the scatter signal profile of the object from the one or more second projection images to produce one or more projection images with a reduced scatter signal; and
reconstruct tomography images based on the projection images with a reduced scatter signal;
wherein the primary beam sampling apparatus comprises an anti-scattering grid comprising a two-dimensional matrix of openings that together define an opening area of 3% or less of a region of interest (ROI) of the area X-ray detector to minimize an additional dose of X-ray radiation to the object when the one or more first projection images of the object are collected; and
wherein the openings are configured to allow transmission of X-ray photons therethrough.

11. The system of claim 10, wherein the area X-ray detector is disposed in a vertical plane substantially perpendicular to a ground and the system is configured such that the object is positioned between the X-ray source array and the area X-ray detector.

12. The system of claim 10, wherein the system is configured to capture a scout view image of the object and determine a number of projection views, angular coverage, X-ray energy, and image radiation dose prior to detecting and collecting the projection images of the object.

13. The system of claim 10 wherein the system is configured to:
monitor physiological gating signals of the object using a physiological monitoring sensor (PMS) attached to the object; and
synchronize acquisition of the projection images with physiological gating signals.

14. The system of claim 13, wherein the detector is configured for detecting projection images upon receiving a signal from the PMS.

15. The system of claim 13, wherein the physiological gating signals comprise respiratory or cardiac signals.

16. The system of claim 10, wherein the system is further configured to:
position the primary beam sampling apparatus between the X-ray source array and the object;
capture the one or more first projection images of the object, wherein the first one or more projection images have reduced or eliminated X-ray photon scatter in one or more sampling regions;
remove the primary beam sampling apparatus from between the X-ray source array and the object;
capture the one or more second projection images of the object, wherein X-ray photon scattering of the second one or more projection images is not reduced;
obtain the scatter signal profile of the object by comparing the one or more first projection images of the object to the one or more second projection images of the object; and
subtract the scatter signal profile from the one or more second projection images to obtain the projection images with a reduced scatter signal.

17. The system of claim 16, wherein:
the anti-scattering grid is disposed in a vertical plane in alignment with and substantially parallel to the X-ray source array and the area X-ray detector; and
the openings of the two-dimensional matrix of openings of the anti-scattering grid run both parallel and perpendicular to the X-ray source array.

18. The system of claim 10, wherein the primary beam sampling apparatus is configured to move horizontally or vertically with respect to a ground.

* * * * *